(12) United States Patent
Berendt et al.

(10) Patent No.: US 12,399,242 B2
(45) Date of Patent: Aug. 26, 2025

(54) MUSCULOSKELETAL RF SURFACE COIL FOR MRI

(71) Applicant: Quality Electrodynamics, LLC, Mayfield Village, OH (US)

(72) Inventors: David Michael Berendt, Aurora, OH (US); Labros Petropoulos, Chardon, OH (US); Xiaoyu Yang, Indiana, PA (US); Tsinghua Zheng, Chesterland, OH (US)

(73) Assignee: Quality Electrodynamics, LLC, Mayfield Village, OH (US)

( * ) Notice: Subject to any disclaimer, the term of this patent is extended or adjusted under 35 U.S.C. 154(b) by 17 days.

(21) Appl. No.: 18/336,176

(22) Filed: Jun. 16, 2023

(65) Prior Publication Data
US 2024/0004007 A1    Jan. 4, 2024

Related U.S. Application Data

(60) Provisional application No. 63/357,064, filed on Jun. 30, 2022.

(51) Int. Cl.
*G01R 33/341*    (2006.01)
*A61B 5/055*    (2006.01)

(52) U.S. Cl.
CPC ........... *G01R 33/341* (2013.01); *A61B 5/055* (2013.01)

(58) Field of Classification Search
CPC ........ G01R 33/341; G01R 33/34007; G01R 33/34084; G01R 33/3415; A61B 5/055; A61B 5/6824; A61B 5/6825; A61B 5/6828; A61B 5/6829
See application file for complete search history.

(56) References Cited

U.S. PATENT DOCUMENTS

| | | |
|---|---|---|
| 4,629,988 A | 12/1986 | Bottomley |
| 4,812,760 A | 3/1989 | Bottomley et al. |
| 5,178,146 A | 1/1993 | Giese |
| 5,197,474 A | 3/1993 | Englund et al. |
| 6,084,411 A | 7/2000 | Giaquinto et al. |
| 6,298,148 B1 | 10/2001 | Cline et al. |
| 7,065,950 B2 | 6/2006 | Zhu et al. |
| 7,365,542 B1 | 4/2008 | Rohling et al. |
| 7,489,133 B1 | 2/2009 | Keidl et al. |
| 7,693,570 B2 | 4/2010 | Green et al. |
| 8,487,620 B2 | 7/2013 | Brown et al. |
| 8,805,477 B2 | 8/2014 | Biber et al. |
| 9,000,766 B2 | 4/2015 | Chu et al. |
| 9,002,431 B2 | 4/2015 | Jones |
| 10,613,164 B2 | 4/2020 | Xie et al. |
| 11,143,723 B2 | 10/2021 | Brown |

(Continued)

*Primary Examiner* — Alexei Bykhovski
(74) *Attorney, Agent, or Firm* — Eschweiler & Potashnik, LLC

(57) ABSTRACT

In some embodiments, the present disclosure relates to a radio frequency (RF) surface coil for a magnetic resonance imaging (MRI) system. The RF surface coil includes a rigid lower member, at least one flexible upper member mechanically coupled to the rigid lower member, and one or more RF coil elements housed by the rigid lower member and the at least one flexible upper member. The at least one flexible upper member is dimensioned and manipulable to substantially conform the one or more RF coil elements to a portion of a patient anatomy to be imaged by the MRI system.

20 Claims, 33 Drawing Sheets

(56) References Cited

U.S. PATENT DOCUMENTS

| | | | |
|---|---|---|---|
| 2008/0204021 A1* | 8/2008 | Leussler | G01R 33/3415 |
| | | | 324/318 |
| 2013/0137969 A1* | 5/2013 | Jones | A61B 5/6804 |
| | | | 600/421 |
| 2015/0323620 A1 | 11/2015 | Yang et al. | |
| 2017/0082705 A1* | 3/2017 | Hou | G01R 33/36 |
| 2017/0143203 A1* | 5/2017 | Yang | A61B 5/004 |
| 2019/0080837 A1* | 3/2019 | Kostakis | H01F 27/29 |
| 2019/0154775 A1* | 5/2019 | Stack | G01R 33/3685 |
| 2020/0326393 A1 | 10/2020 | Johnson et al. | |
| 2021/0072330 A1 | 3/2021 | Berendt, Jr. et al. | |
| 2021/0208220 A1* | 7/2021 | Brown | G01R 33/3415 |

\* cited by examiner

MUSCULOSKELETAL RF SURFACE COIL FOR MRI

REFERENCE TO RELATED APPLICATION

This application claims the benefit of U.S. Provisional Application No. 63/357,064, filed on Jun. 30, 2022, the contents of which are hereby incorporated herein by reference in their entirety.

BACKGROUND

Magnetic resonance imaging (MRI) involves the transmission and receipt of radio frequency (RF) energy. RF energy may be transmitted by an RF coil to create a $B_1$ field that rotates a net magnetization. Further, resulting magnetic resonance (MR) signals may be received by an RF coil to detect precessing transverse magnetization. Thus, RF coils may be transmit (Tx) coils, receive (Rx) coils, or transmit and receive (Tx/Rx) coils.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
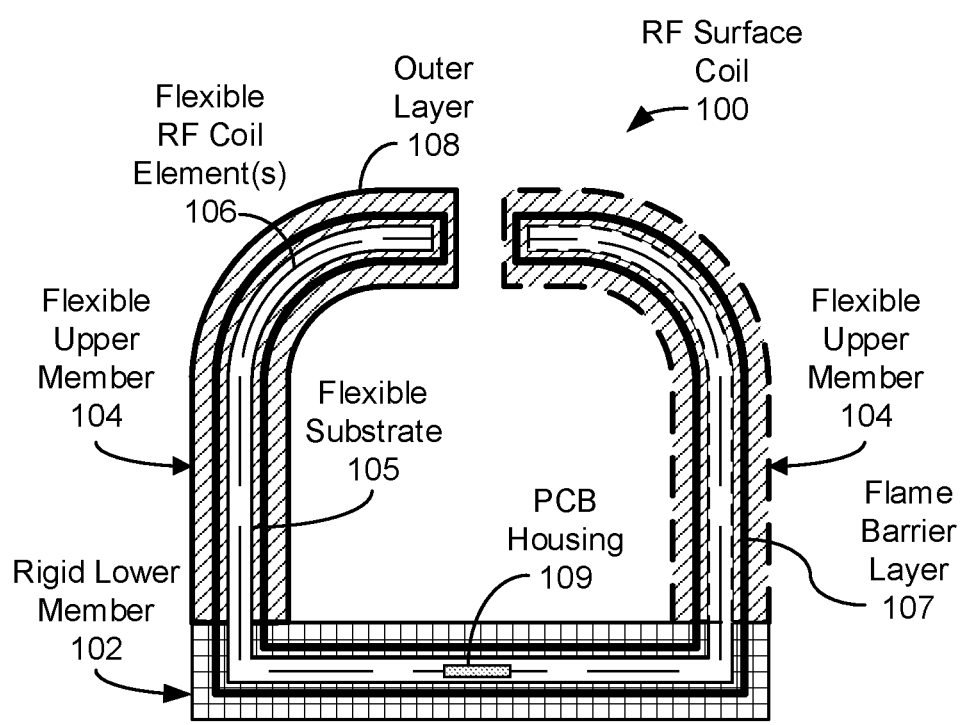
FIG. 1 illustrates a cross-sectional schematic view of some embodiments of an RF surface coil for an MRI system.
Figure 2A:
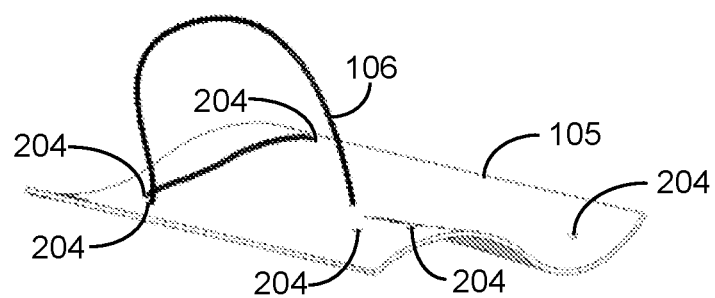
FIGS. 2A-2D illustrate views of some embodiments of an RF coil element being woven into a flexible substrate.
Figure 2B:
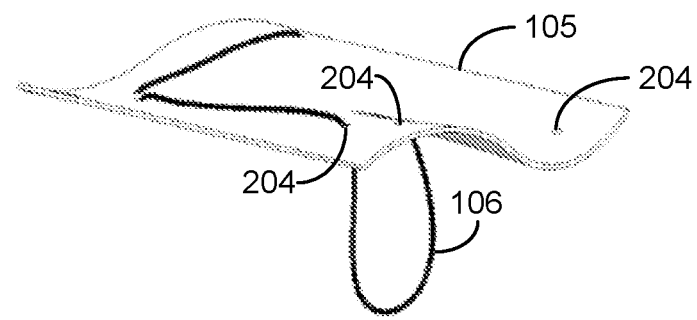
Figure 2C:
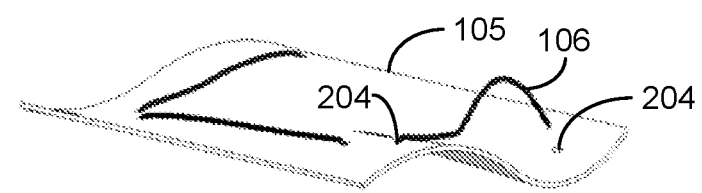
Figure 2D:
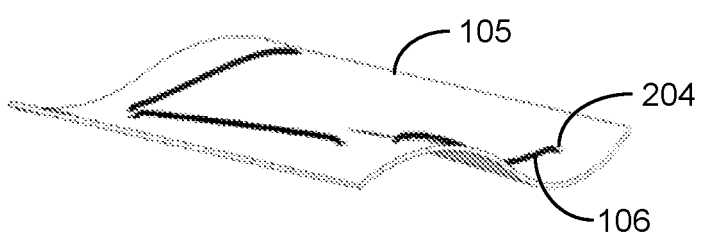

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purposes of simplicity and clarity and does not in itself dictate a relationship between the various embodiments and/or configurations discussed.

Further, spatially relative terms, such as "beneath," "below," "lower," "above," "upper," "lower," and the like, may be used herein for ease of description to describe one element or feature's relationship to one or more other elements or features as illustrated in the figures. The spatially relative terms are intended to encompass different orientations of the device in use or operation in addition to the orientation depicted in the figures. The apparatus may be otherwise oriented (e.g., rotated 90 degrees or at other orientations), and the spatially relative descriptors used herein may likewise be interpreted accordingly.

The present disclosure relates to magnetic resonance imaging (MRI), particularly regarding the use of a local radio-frequency (RF) surface coil in conjunction with an MRI apparatus or system to create a diagnostic image of a region of interest of a patient (e.g., human or other animal) anatomy. In some embodiments, the RF surface coil may include at least one flexible upper member coupled to a rigid lower member. Also, in some embodiments, the RF surface coil may include one or more flexible RF coil elements (e.g., housed in the at least one flexible upper member and possibly the rigid lower member). In addition, the at least one flexible member may be dimensioned and manipulable to substantially conform the one or more flexible RF coil elements to a portion of a patient anatomy to be imaged by the MRI system.

As a result of at least some embodiments, the RF surface coil may facilitate the placement of the one or more flexible RF coil elements within close proximity to the portion of the patient anatomy to be scanned, thus potentially increasing the quality (e.g., resolution, clarity, etc.) of the resulting image.

With reference to FIG. 1, a cross-sectional schematic view of some embodiments of an RF surface coil 100 for an MRI system according to aspects of the present disclosure is provided. Some aspects of an example MRI system are described in greater detail below in conjunction with FIGS. 28 and 29. In FIG. 1, the RF surface coil 100 may include a rigid lower member 102 mechanically coupled to at least one flexible upper member 104. While FIG. 1 indicates the presence of at least one, and possibly two, flexible upper members 104, greater than two flexible upper members 104 may be present in other embodiments.

As depicted in FIG. 1, one or more flexible RF coil elements 106 may be housed by the rigid lower member 102 and the at least one flexible upper member 104. In other embodiments, the one or more flexible RF coil elements 106 may only be housed by the at least one flexible upper member 104. Further, in some embodiments, the at least one flexible upper member 104 may be dimensioned and manipulable to substantially conform the one or more flexible RF coil elements 106 to substantially conform the one or more flexible RF coil elements to a portion of a patient anatomy to be imaged by the MRI system (e.g., a knee, hand, wrist, elbow, shoulder, hip, knee, ankle, foot, and so on). In at least some embodiments, the RF surface coil 100 may be employed as a receive (Rx) antenna to receive RF pulses produced by the tissue of the patient anatomy in response to the operation of the MRI system to create images of that tissue to aid in the diagnosis of medical conditions. Moreover, the placement of the one or more flexible RF coil elements 106 in close proximity to the portion of the patient anatomy to be imaged may improve the quality of the created image by way of increased signal-to-noise ratio (SNR), which may be of significant importance, particularly when the features of the anatomy portion to be imaged are relatively small.

More generally, various embodiments of the present disclosure may represent one or more of at least three advances in surface coil design to facilitate close placement of the one or more flexible RF coil elements relative to the patient anatomy: (1) some or all of the one or more flexible RF coil elements in the surface coil may mechanically flex in order to conform to the varying sizes of anatomies of multiple patients, (2) one or more mechanical features may position the surface coil stably and consistently relative to the MRI system, and (3) restraint features may retain the one or more flexible RF coil elements against the portion of the patient anatomy being imaged.

In some embodiments, the one or more flexible RF coil elements 106 may be affixed to a flexible substrate 105, as depicted in FIG. 1. This arrangement may permit a plurality of element geometries and element patterns, as discussed below in connection with FIGS. 4A-4H and FIGS. 6A-6E. The flexible substrate 105 may also be referred to as a mechanical substrate, a flexible mechanical structure, or the like hereafter. Additionally, supporting components (e.g., electronic components, such as capacitors, resistors, preamplifiers, PIN diodes, and/or additional signal processing components) and/or housing components may be affixed to the flexible substrate 105. The housing components may be or include, for example, a printed circuit board (PCB) housing 109 (e.g., a rigid enclosure to house the supporting components). The supporting components may include, for example, components intended to amplify the RF signal and/or to decouple the one or more flexible RF coil elements 106 from each other.

In some embodiments, the flexible substrate 105 may be constructed from foam, nylon fabric, thermoplastic polyurethane foil (TPU), aramid (aromatic polyamide) wool or matting, or other material that provides flexibility along several bending axes simultaneously while capable of being subjected to tensile forces without stretching significantly. The flexible substrate 105 may secure and position the conductors (e.g., loops) of the one or more flexible RF coil elements 106, thus controlling the positions of the conductors with respect to each other and possibly ensuring that the attenuation of each conductor is maintained. Affixing the conductors of the one or more flexible RF coil elements 106 to the flexible substrate 105, together with affixing the PCB housing 109 that houses one or more supporting components (e.g., decoupling, preamplifier, and other circuits associated with the one or more flexible RF coil elements 106) to the flexible substrate 105, may substantially ensure that forces due to bending the one or more flexible RF coil elements 106 are not transferred to the supporting components.

In at least some embodiments, such methods of construction of the RF surface coil 100 may be superior to the use of flexible (e.g., polyimide or polyamide) circuit boards, which may include a conductive material (e.g., copper) inlaid onto a pliant, flexible material (e.g., Kapton® by DuPont de Nemours, Inc.), thus creating a circuit board capable of having componentry soldered thereto. A surface coil constructed in this conventional manner is generally capable of flexing in a way that is consistent with a developable surface, which is typically cylindrical or conical in the case of a flexible surface coil. While it is possible to create a flexible PCB substrate that permits simultaneous flexing in multiple axes that is consistent with a non-developable surface (e.g., a dome shape or saddle shape), limitations are typically imposed by the material that prevent a surface coil from being used in a standard clinical environment with a sufficient degree of reliability and repeatability.

Moreover, the RF surface coil 100 embodiments discussed herein may provide a lightweight and flexible surface coil capable of conforming to a patient's shape while protecting the one or more flexible RF coil elements 106 and associated components from stresses that result from repeated flexing. Such embodiments may help deter the reduced performance and shortened working life of RF coil elements and associated components of conventional surface coils, which may become damaged due to the metal fatigue caused by the stresses encountered by the conductive portions of the RF coil element in such surface coils.

Also, in some embodiments, as shown in FIG. 1, the flexible substrate 105, with the one or more flexible RF coil elements 106 and associated components assembled thereto, may be covered with one or more separate flame barrier layers 107 (e.g., meta-aramid wool or the like). The one or more separate flame barrier layers 107 may be applied to the upper and lower surfaces of the flexible substrate 105 to provide a flame-retardant barrier between the flexible substrate 105 (and associated one or more flexible RF coil elements 106) and the patient to meet flammability requirements. In some embodiments, the flame barrier layer(s) 107 may be made from para-aramid, polyester, or other fabrics or materials treated with flame retardant chemicals, which may also provide a barrier that meets the flammability requirements.

Additionally, in FIG. 1, in some embodiments, the flexible substrate 105, the one or more flexible RF coil elements 106, with associated components, internal cable assembly, rigid enclosure (e.g., the PCB housing 109), and the flame barrier layer(s) 107, may be covered in an outer layer 108 of material. Such material, in some embodiments, may be made of a urethane film adhered to a cloth backer fabricated from nylon, polyester, or another material. The outer layer 108 may provide a fluid ingress barrier for the RF surface coil 100 in addition to serving as the patient contact surface of the RF surface coil 100.

Several ways of attaching the one or more flexible RF coil elements 106 to the flexible substrate 105 of RF surface coil 100 of FIG. 1 are possible. For example, FIGS. 2A-2D illustrate views of some embodiments of a flexible RF coil element 106 being woven into the flexible substrate 105. As shown, the flexible substrate 105 may define a number of holes 204 through which the flexible RF coil element 106 is threaded to attach the flexible RF coil element 106 to the flexible substrate 105.

In some embodiments, a flexible RF coil element 106 may be attached to the flexible substrate 105 by overlaying a retaining member fabricated from the same or similar material type as the flexible substrate 105, and then welding the retaining member to the flexible substrate 105 using either RF or ultrasonic energy to bond the retaining member to the flexible substrate 105, such that the flexible RF coil element 106 are fixed in place.

In some embodiments, the one or more flexible RF coil elements 106 may be fastened to the flexible substrate 105 by sewing the element material to the flexible substrate 105.

Figure 3A:
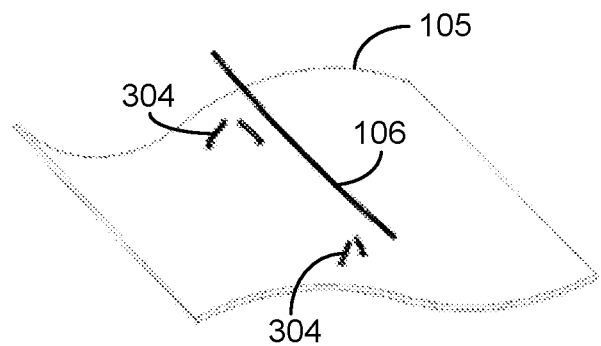
FIGS. 3A-3C illustrate views of some embodiments of an RF coil element being placed onto a flexible substrate and fastened thereto.
Figure 3B:
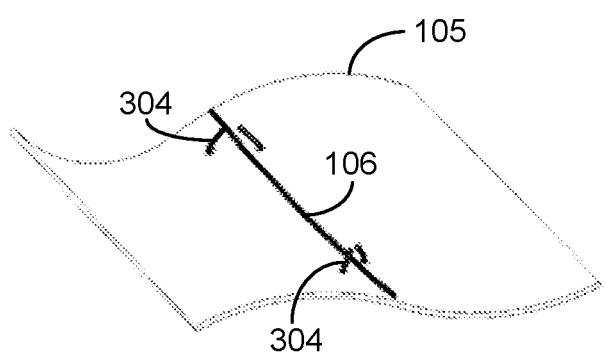
Figure 3C:
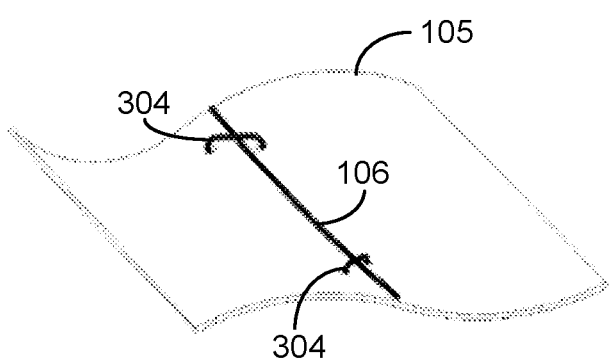

FIGS. 3A-3C illustrate views of some embodiments of a flexible RF coil element 106 being placed on a flexible substrate 105 (as depicted in FIG. 3A) and fastened to the flexible substrate 105 using a secondary fastener 304, such as a clip, wire tie, rivet, or the like (e.g., as shown in FIGS. 3B and 3C). In yet another embodiment, the one or more flexible RF coil elements 106 may be fastened to the flexible substrate 105 using an adhesive, such as hot melt glue or the like, that is applied in several locations along the one or more flexible RF coil elements 106. Further, any combination of these embodiments may be used to construct the desired element shape.

In some embodiments, the flexible substrate 105 may be fabricated from a highly flexible material. In some embodiments, the flexible substrate 105 material may be Nomex® meta-aramid wool (by DuPont de Nemours, Inc.), polyester wool, or the like. Strategically located hole patterns (e.g., patterns of holes 204 as illustrated in FIGS. 2A-2D) may be provided as fastening locations for housing components that contain supporting components of the surface coil (e.g., preamplifiers, decoupling circuits, and so on). The holes 204 may be arranged such that when the conductor (e.g., loop) of the flexible RF coil element 106 is passed through the holes 204, the position and size of the flexible RF coil element 106 is maintained by the flexible substrate 105 due to being constrained by the positions of the holes 204, as discussed above in conjunction with FIGS. 2A-2D. In other embodiments, holes may be provided as a means to fasten the one or more flexible RF coil elements 106 to the flexible substrate 105 with a clip, wire tie, rivet, or the like, as described above in connection with FIGS. 3A-3C.

In some embodiments, the flexible RF coil element 106 may be formed in part by depositing conductive ink onto the flexible substrate 105, whereby the ink defines the conductor (e.g., loop) of the flexible RF coil element 106. In this embodiment, the supporting components (e.g., electronics) may be connected to the flexible substrate 105 and the conductor of the flexible RF coil element 106 by either soldering the supporting components to the conductor or by mechanically fastening the supporting components to the conductor of the flexible RF coil element 106 and the flexible substrate 105 with one or more screws, rivets, or the like.

In some embodiments, the flexible RF coil element 106 may include a coaxial cable, which may be weaved into and out of the flexible substrate 105, as shown in FIGS. 2A-2D. Additional embodiments may include a flexible RF coil element 106 formed by a flexible circuit board fabricated from copper and amide (e.g., Kapton®). By using the holes 204 as a means of position and control over the location of the coaxial cable, the flexible RF coil element 106 may be held in a stable location by the flexible substrate 105.

Figure 4A:
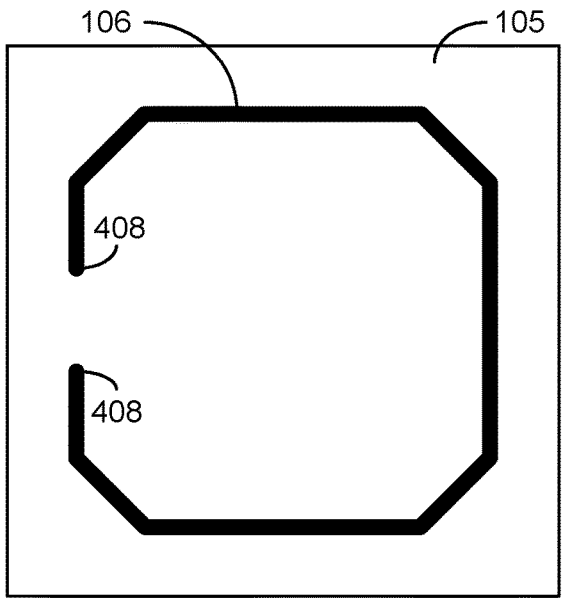
FIGS. 4A-4H illustrate top views of some embodiments of various shapes of an RF coil element attached to a flexible substrate.
Figure 4B:
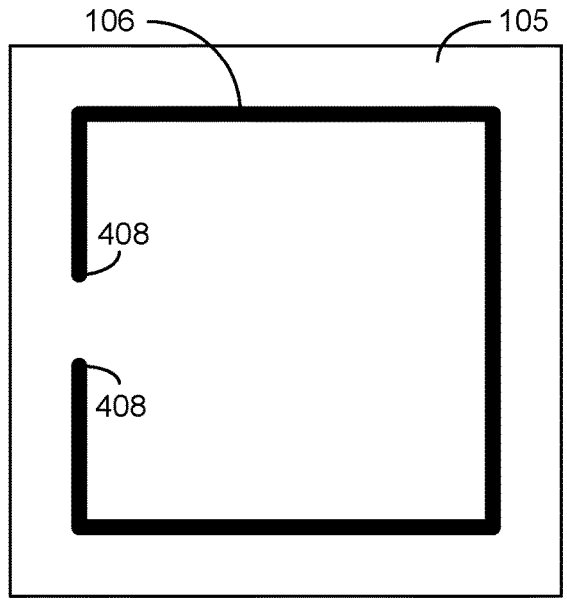
Figure 4C:
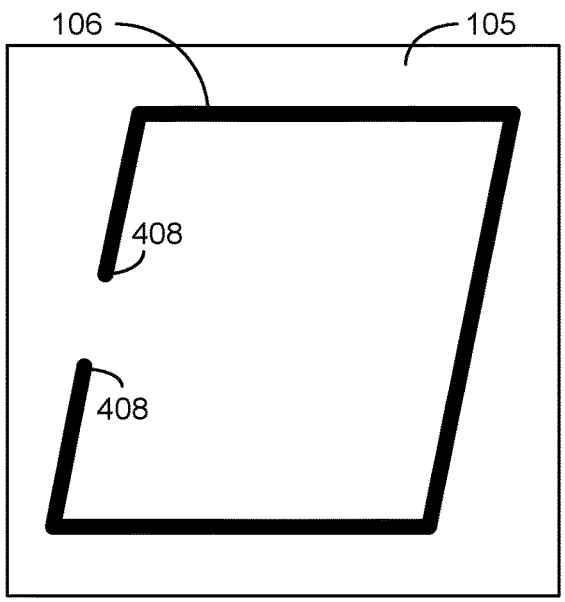
Figure 4D:
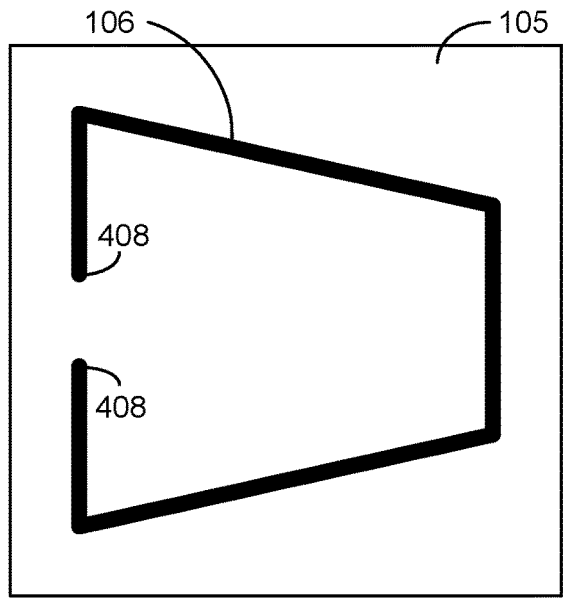
Figure 4E:
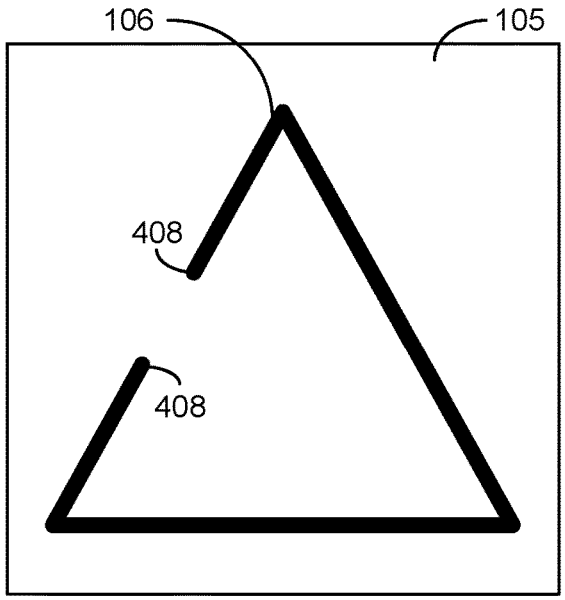
Figure 4F:
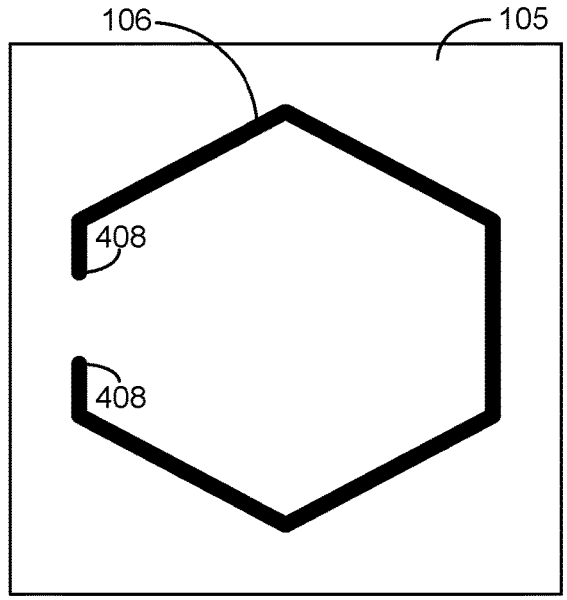
Figure 4G:
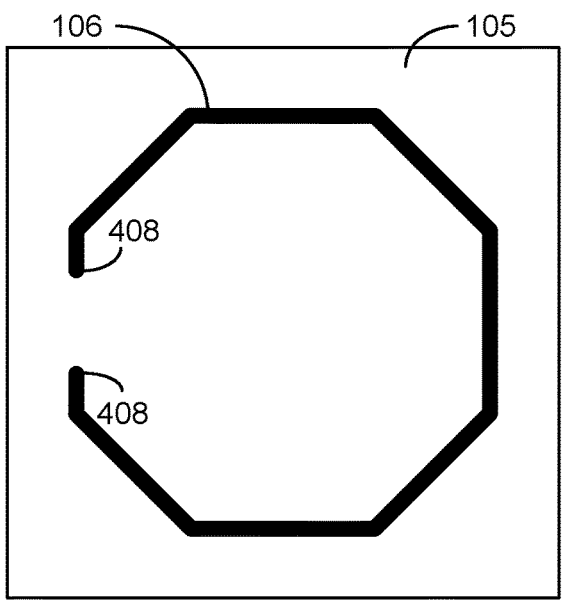
Figure 4H:
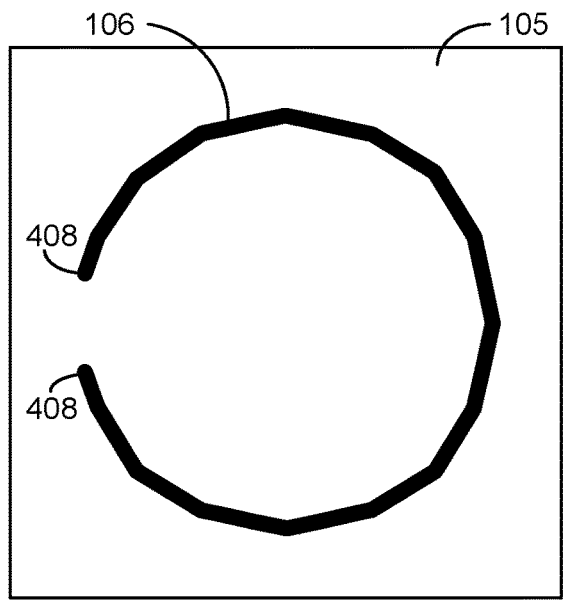

In at least some embodiments, the conductor of a flexible RF coil element 106 may be configured in a loop having ends 408, formed in one of a variety of shapes, and attached to the flexible substrate 105, as depicted in FIGS. 4A-4H. In some embodiments, such a loop may be square-shaped with chamfered corners, as shown in FIG. 4A. In some embodiments, the loop may resemble any quadrilateral shape, such as a rectangle, as shown in FIG. 4B; a parallelogram, as shown in FIG. 4C; a trapezoid, as shown in FIG. 4D; a triangle, as shown in FIG. 4E; a hexagon, as shown in FIG. 4F; an octagon, as shown in FIG. 4G; a higher-order polygon which approximates a circle (e.g., in a piecewise-linear manner), as shown in FIG. 4H; or some other polygon having a greater or lesser number of sides than the aforementioned polygons. Additional embodiments may also include saddle-shaped flexible RF coil elements 106, and may be used in conjunction with any type of loop element, including, but not limited to, the element types listed above.

Figure 5A:
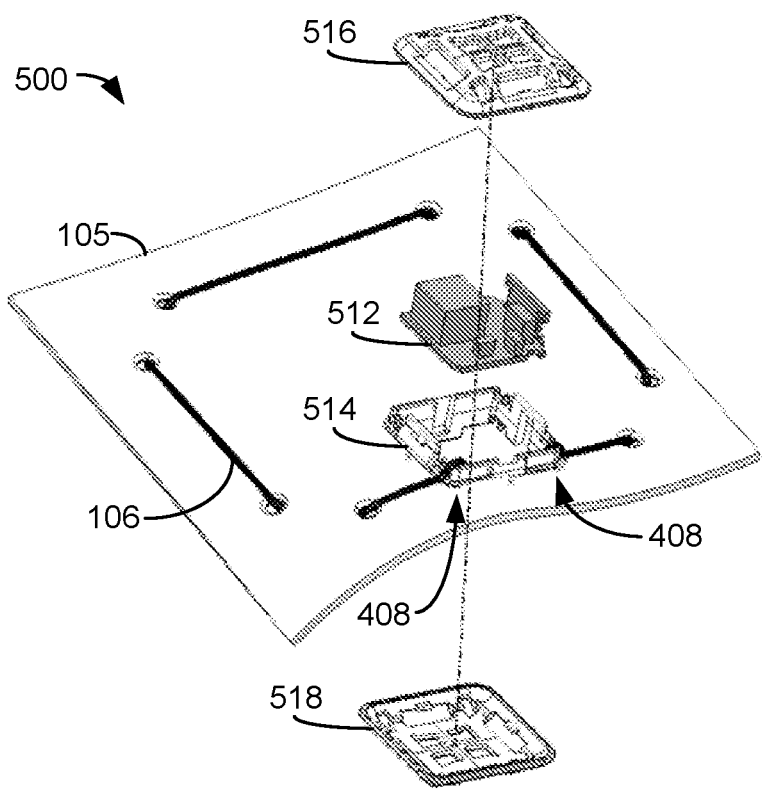
FIGS. 5A and 5B respectively illustrate an exploded view and an assembled view of some embodiments of a housing and associated printed circuit board (PCB) for an RF coil element attached to a flexible substrate.
Figure 5B:
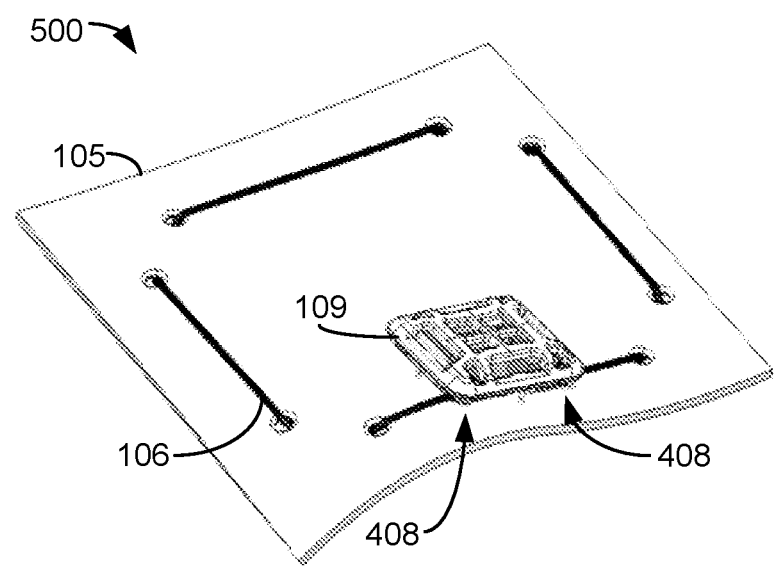

In some embodiments, a rigid housing (e.g., the PCB housing 109 of FIG. 1) may encapsulate and position a rigid PCB, which may include the supporting components and any other electrical components of the flexible RF coil element 106 that are used to amplify the RF signal before transmitting the signal to a system cable. FIGS. 5A and 5B respectively illustrate an exploded view and an assembled view of some embodiments of the PCB housing 109 (e.g., including a top portion 516 and a bottom portion 518) and associated PCB 512 (e.g., seated in a chassis 514) to provide an electrical connection between the PCB 512 and ends 408 of a flexible RF coil element 106 attached to a flexible substrate 105. Additional components within the PCB housing 109 may include decoupling circuitry and an input balun. The PCB housing 109 may be fastened to the flexible substrate 105 using a fastening component, including, but not limited to, a rivet or screw. Other mechanical enclosures or structures, or electrical components, may be mounted in addition to the aforementioned components in other embodiments.

In some embodiments, the flexible substrate 105, with the one or more flexible RF coil elements 106 and associated components assembled thereto, may be covered with one or more flame barrier layers 107, as described above in connection with FIG. 1. In addition, in some embodiments of the overall assembly 500, the flexible substrate 105, one or more flexible RF coil elements 106 with associated components, internal cable assembly, rigid enclosures (e.g., the PCB housing 109), and one or more flame barrier layers 107 may be covered in an outer layer 108, as discussed above.

In some embodiments, the assembly 500 may enable a plurality of flexible RF coil elements 106 to be employed on a single flexible substrate 105. In some embodiments, the flexible RF coil elements 106 may be arranged in an array, and each may be able to acquire a signal from the anatomy being imaged. Further, the resulting signals from the flexible RF coil elements 106 may be combined in a way that enhances the overall image.

Additionally, in some embodiments, different RF surface coils 100 may be used to obtain images from different locations of the body of the patient. These surface coils may use flexible RF coil elements 106 of differing sizes or arrangements based on the needs of the imaging application. For example, a wrist application may depend on flexible RF coil elements 106 of small size compared to other musculoskeletal applications to obtain a high SNR of the relatively small features (e.g., muscles, ligaments, etc.) in the wrist, which may depend on a high image resolution to obtain an accurate diagnosis.

Figure 6A:
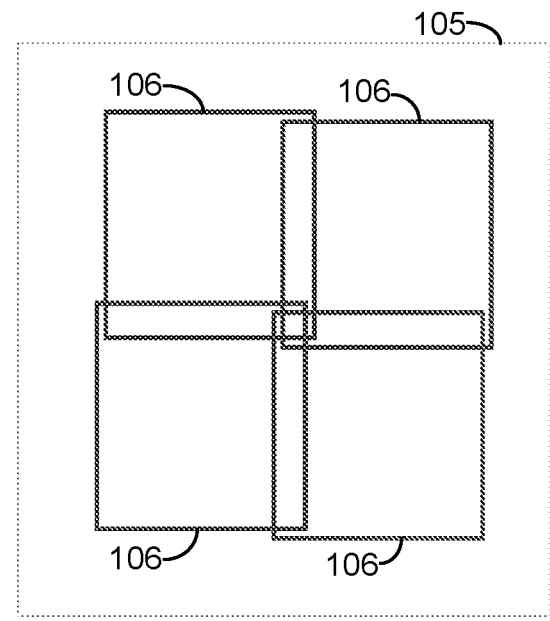
FIGS. 6A-6E illustrate top views of some embodiments of various RF coil element patterns.
Figure 6B:
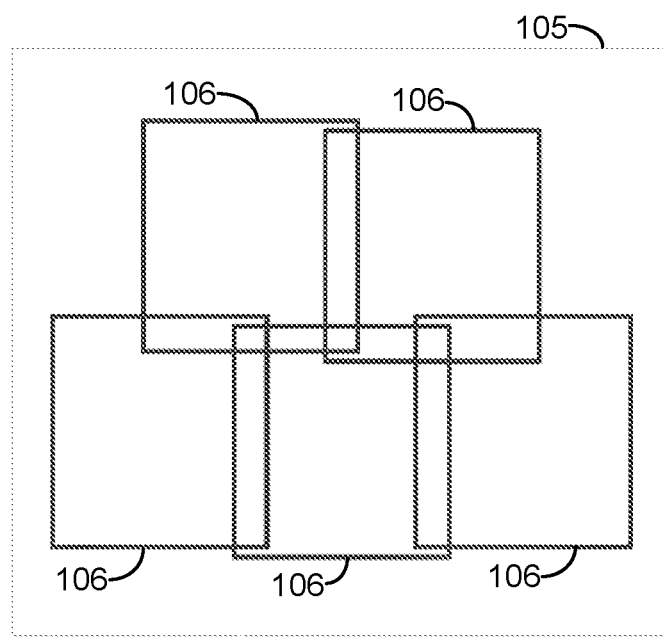
Figure 6C:
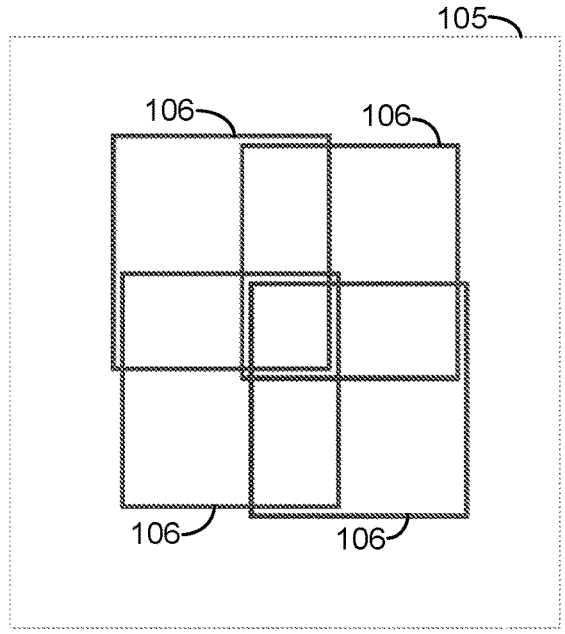
Figure 6D:
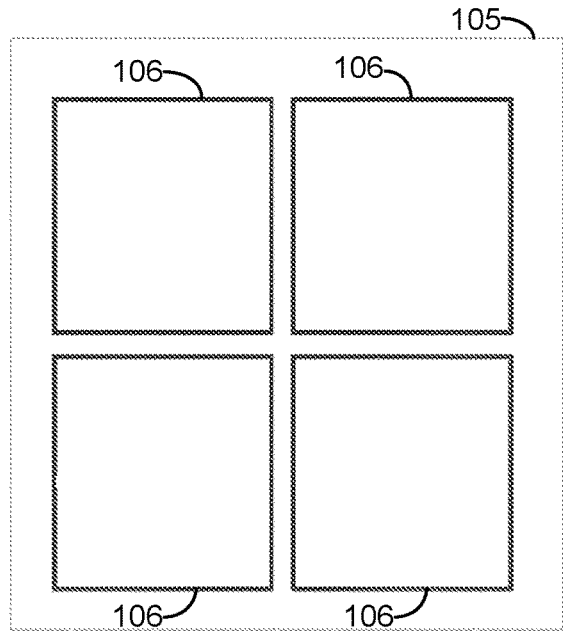
Figure 6E:
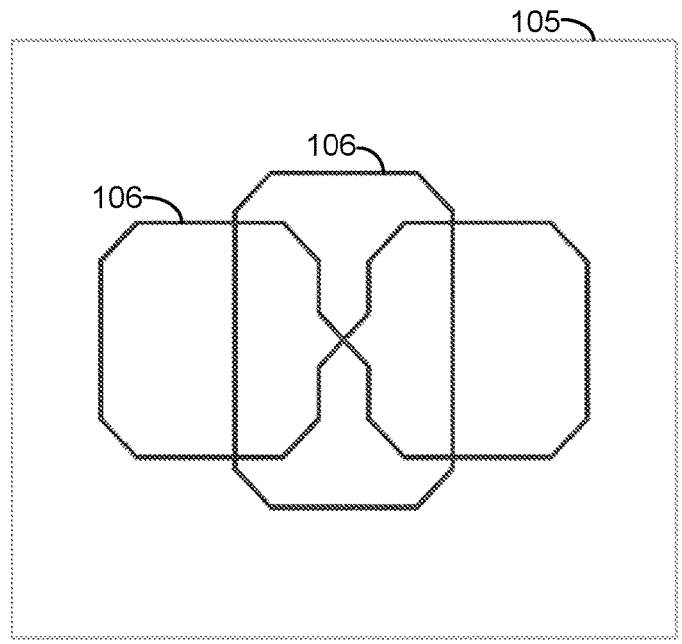

FIGS. 6A-6E illustrate top views of some embodiments of various RF coil element patterns. For example, FIG. 6A illustrates some embodiments of a coil element configuration having an overlapped pattern of flexible RF coil elements 106 that are attached to a flexible substrate 105 and positioned in a manner such that flexible RF coil elements 106 located in an adjacent manner horizontally create a row of flexible RF coil elements 106, and flexible RF coil elements 106 located in an adjacent manner vertically create a column of flexible RF coil elements 106. In another embodiment, as shown in FIG. 6B, a coil element configuration may include the flexible RF coil elements 106 that are arrayed such that each flexible RF coil element 106 in a row is overlapped by the adjacent flexible RF coil element 106 in the same row, and each row is offset in the transverse (horizontal) axis by a certain amount (e.g., 50% of the coil element width) from the row above and/or the row below. In another embodiment, as illustrated in FIG. 6C, a coil element configuration may exhibit a large range of flexible RF coil element 106 positioning, such as a high degree of flexible RF coil element 106 overlapping. In other embodiments, such as depicted in FIG. 6D, a coil element configuration may exhibit underlapping (e.g., non-overlapping) of rows of flexible RF coil elements 106, underlapping (e.g., non-overlapping) of columns of flexible RF coil elements 106, or a combination thereof. In other embodiments, as shown in FIG. 6E, a coil element configuration may include a "loop and saddle" configuration, whereby any of the aforementioned flexible RF coil element shapes (e.g., a chamfered RF coil element shape of FIG. 4A) may be located coincident with a saddle-shaped flexible RF coil element 106. Other possible numbers, shapes, and relative positioning of flexible RF coil elements 106 may be utilized in other embodiments.

In some embodiments, an additional aspect of the RF surface coil 100 (FIG. 1) may be that a flexible RF coil element 106 array may be assembled with a rigid or semi-rigid structure (e.g., rigid lower member 102) to constrain that portion of the array rigidly, such that the form of the RF surface coil 100 permits a scan of a patient anatomy, such as a knee, foot, ankle, hand, wrist, elbow, shoulder, or other anatomy. In some embodiments, the flexible RF coil element 106 array may be configured in a form that is a rectangle in its layout appearance. The flexible RF coil element 106 array may also be configured to have flaps or other tabs, which may permit element overlaps and forms that, when flexed into a three-dimensional shape, may be optimized for a specific anatomy.

At least some embodiments of an RF surface coil 100 included in the present disclosure may further include or be associated with a structural component (referred to herein as a "baseframe") that interfaces with a patient table of an MRI system. The baseframe may include two primary sets of features: (1) a set of features that interfaces with the patient table; and (2) a set of features that positions the RF surface coil 100 in a fixed location and orientation relative to the MRI system. In some embodiments, the table-interfacing features may include an external profile that matches the patient table such that the baseframe may attach to the patient table profile in multiple locations and/or orientations relative to the patient table. The table-interfacing features may be constructed of one or more rigid materials, such as polymers, metals, urethanes, foams, or the like, or some combination thereof, of sufficient strength and rigidity to support the weight of equipment and at least a portion of patient's weight.

The baseframe and/or the rigid lower member 102 may also include coil-positioning features or structures to mechanically retain the rigid lower member 102 in a range of positions along the x-axis of the MRI system (e.g., laterally across a width of the patient table) in addition to permitting the rigid lower member 102 to be held in a range of orientations about the y-axis (e.g., up and down vertically, normal to a top surface of the patient table).

In some embodiments, the coil-positioning features of the baseframe and/or the rigid lower member 102 may possess a mechanical retention feature that locks the position and/or orientation of the RF surface coil 100 (e.g., via the rigid lower member 102) relative to the table-interfacing features of the baseframe. In some embodiments, the retention feature of the coil-positioning structures may include a lever or knob that, when rotated, turns a cam mechanism that disengages a set of retaining teeth from a mating set of teeth or similar structures of the baseframe, which may allow the coil-positioning structure to move relative to the table-interfacing features. When the lever or knob is rotated back to its original (locking) position, the retention teeth are re-engaged to the retention features of the baseframe, thus causing the coil-positioning structure to be retained in its current position and orientation.

In some embodiments, the coil-positioning structure may include features that detachably retain a number of different surface coils. The retention features may include one or more latching tabs that fasten the rigid lower member 102 of the RF surface coil 100 to the coil-mounting structure of the baseframe. Some embodiments of the retention feature may include one or more latching tabs that move such that the RF surface coil 100 is mechanically released from the baseframe.

In some embodiments, the coil-positioning features may support the rigid lower member 102 of the RF surface coil 100. Further, in some embodiments, the rigid lower member 102 of the RF surface coil 100 may be constructed from a rigid polymer that houses electrical circuitry of the RF surface coil 100. The rigid lower member 102 of the RF surface coil 100 may support the portion of the patient anatomy that is undergoing a scan procedure. Also, in some embodiments, the rigid lower member 102 may be shaped to accommodate (e.g., approximately match a shape of) a particular portion of the patient anatomy to be imaged, such as a knee, ankle/foot, wrist/hand, and so on. The rigid lower member 102 may further include mounting features for a cable assembly that interfaces with the MRI system, as well as mounting features for the one or more flexible upper members 104.

Described hereinafter are several embodiments of the RF surface coil 100 of FIG. 1 directed to imaging particular anatomies of a patient. For example, FIGS. 7A-12B illustrate views of some embodiments of an RF surface coil 100A for imaging a knee anatomy of a patient. FIGS. 13A-16B depict view of some embodiments of an RF surface coil 100B for imaging a foot and ankle anatomy of a patient. FIGS. 17A-20B illustrate views of some embodiments of an RF surface coil 100C for imaging a hand and wrist anatomy of a patient. FIGS. 21A-26C illustrate views of some embodiments of an RF surface coil 100D for imaging a more general musculoskeletal region of a patient anatomy, such as a shoulder, elbow, torso, or hip anatomy.

Figure 7A:
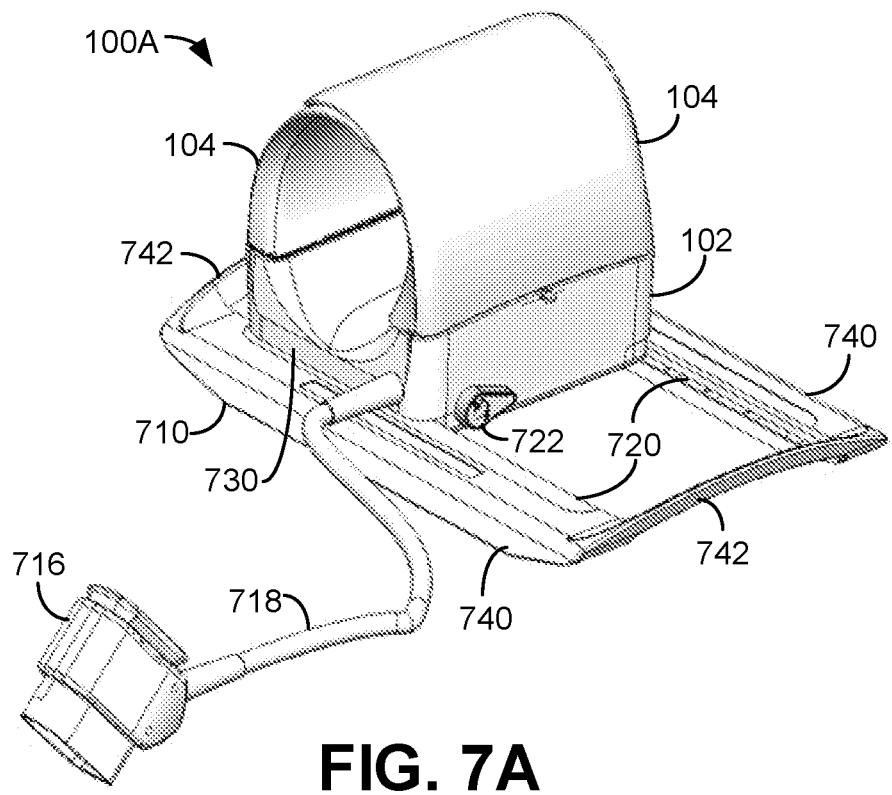
FIGS. 7A and 7B illustrate views of some embodiments of an RF surface coil for scanning a knee anatomy, in which the RF surface coil is configured to scan a patient's right and left knee, respectively.
Figure 7B:
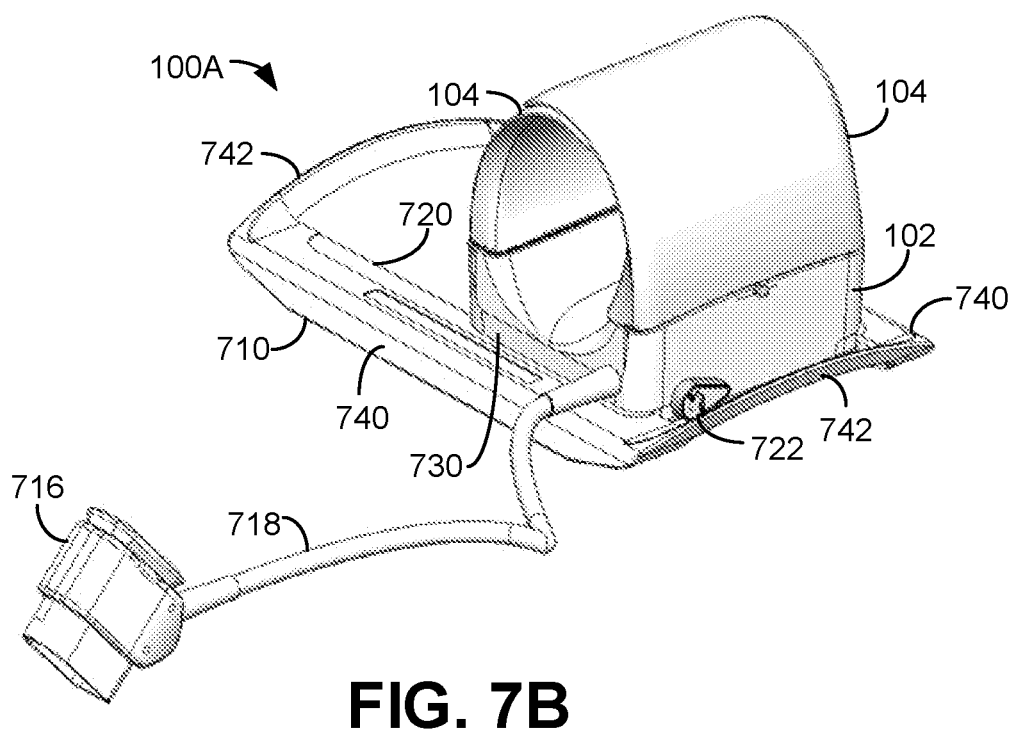

With respect to knee imaging, FIGS. 7A and 7B illustrate views of some embodiments of an RF surface coil 100A with a flexible RF coil element array for scanning a knee anatomy, in which the RF surface coil 100A is configured to scan a patient's right and left knee, respectively. More specifically, RF surface coil 100A may include two flexible upper members 104 attached to a rigid lower member 102. In some embodiments, the flexible upper members 104 and the rigid lower member 102 collectively encompass or enclose one or more RF coil elements attached to a flexible substrate (e.g., as described above in conjunction with FIGS. 2A-6E, but not explicitly shown in FIGS. 7A and 7B), thus being configured to surround a knee to be imaged. In some examples, a housing carrying supporting components (e.g., the PCB housing 109 of FIGS. 1, 5A, and 5B) may be located in the rigid lower member 102 or the flexible upper members 104.

In some embodiments, a system cable 718 may also be provided that is electrically coupled to the RF coil elements (e.g., through the supporting components for the RF coil elements) via the rigid lower member 102. The system cable 718 may also include a system cable connector 716 for interfacing with the MRI system.

As indicated in FIGS. 7A and 7B, the rigid lower member 102 may be mechanically coupled to a baseframe 710, as described above (e.g., by way of a coil-positioning structure 730). In some embodiments, the coil-positioning structure 730 (e.g., retention teeth or similar features) may be engaged and disengaged by way of rotating a knob or lever 722 (e.g., counterclockwise). When disengaged, the rigid lower member 102 may be translated along a top surface of the baseframe 710 (e.g., via opposing rails 720 of the baseframe 710). After such translation, the coil-positioning structure 730 may be reengaged by rotating the lever 722 (e.g., clockwise). For example, FIG. 7A depicts the rigid lower member 102 in a position commensurate with imaging a right knee of a patient, and FIG. 7B shows the rigid lower member 102 in a position appropriate for imaging the left knee of a patient.

In some embodiments, the baseframe 710 of the RF surface coil 100A may be a single structural component for supporting and adapting the RF surface coil 100A to an MRI system patient table. The baseframe 710 may include a table interface structure made from materials such as foams, plastics, metals, or urethanes and a coil-positioning structure made from materials such as foams, plastics, metals, or urethanes. The table interface structure may support the weight of the equipment and at least a portion of the patient's weight and may mate to the defining features of the MRI system patient table. Examples of these mating patient table features are table widths where the table has two parallel walls that run along the axis of the bore, tables with curvature, or tables with locating features, such as pins, keys, steps or groves. Various embodiments of the table interface structure may be adaptable to any system table that currently exists or may exist on future systems, many of which possess a unique patient table and associated interface structure, even when compared to other patient tables provided by the same manufacturer.

In some embodiments, the baseframe 710 includes features that interface directly with the patient table's various mounting features. As shown in FIGS. 7A and 7B, the table-interfacing structure may include two long parallel sides 740 that are at a set distance from one another to mate with the MRI system patient table's walls. The table interfacing structure of this embodiment may also have two shorter parallel sides 742 that are at a set distance that mate to the side walls of a wide MRI system patient table. In another embodiment, the baseframe 710 may include chamfered or curved surfaces along the underside of the baseframe 710 (not shown in FIGS. 7A and 7B) that interface with a patient table with a curved or angled profile.

While the baseframe 710 and corresponding features are described above with respect to the RF surface coil 100A, the baseframe 710 and/or other baseframes may be employed in connection with other RF surface coils described hereinafter to interface the RF surface coils with a patient table of an MRI system.

In some embodiments, the coil-positioning structure of the RF surface coil 100A (e.g., the coil-positioning structure 730 of FIGS. 7A and 7B) is the mating structure for mounting, orienting, and final positioning of the RF surface coil 100A. In some embodiments, the RF surface coil 100A positioning features may be a part of the baseframe 710, the rigid lower member 102, or an adaptor component that attaches to the rigid lower member 102 of the baseframe 710. The adapter component may be designed to contain features such as a locking mechanism (e.g., a sliding and/or rotational mechanism) that positively locates the RF surface coil 100A relative to the baseframe 710. This combination of components may allow the structure to adapt to locate a plurality of RF surface coils appropriately in the MRI system bore. In some embodiments, the orientation and location of the RF surface coil 100A can also be changed by rotating or flipping the baseframe 710 relative to the patient table. Such a configuration may also allow for the RF surface coil 100A to be positioned for scanning the left side knee (e.g., FIG. 7B) or right side knee (e.g., FIG. 7A) of the patient by flipping or rotating the baseframe 710 to orient the RF surface coil 100A for the appropriate application.

Various embodiments of the present disclosure may thus allow end users, such as hospitals, clinics, imaging centers, and mobile imaging centers, to change between multiple surface coil types, to re-position the surface coils to the desired position to accommodate patients of various sizes, and to conduct a variety of types of MRI scans. Accordingly, such a configuration may reduce the number of baseframes 710 needed for various MRI systems and the various RF surface coils to be employed. Correspondingly, such a configuration may also reduce the number of operational steps required to change between the various RF surface coils (e.g., RF surface coil 100A) and their orientations relative to the patient table, which typically would involve dismounting the surface coil from a current baseframe, removing the current baseframe from the patient table, locating the required baseframe, placing the required baseframe on the patient table, and remounting the surface coil to the base.

In some embodiments, the table interface structure and the coil-positioning structure of the baseframe 710 may be contained within a single part or be made of multiple parts. The table interface structure may be covered with materials such as a urethane-coated nylon fabric, paint, polymer coating, or may remain in an uncoated state. Such coating may give the structure a soft-touch feel and provide a biocompatible contact surface. Non-biocompatible surfaces may be used in certain applications.

In some embodiments, the table interface structure may be formed from expanded polypropylene (EPP) foam or other materials that are cut to fit the intended patient tables. The surfaces of the table interface structure may be made with a process such as machining, molding, and forming to accept mating features of other tables, such as beveled or curved edges. The table interfacing structure may also be configured to accept a coil-positioning structure 730 that connects the rigid lower member 102 of the RF surface coil 100A to the baseframe 710. The coil-positioning structure 730 may be designed to utilize a plurality of parts to capture the EPP foam table interface structure, without fastening directly to the foam, when fastened together.

Figure 8A:
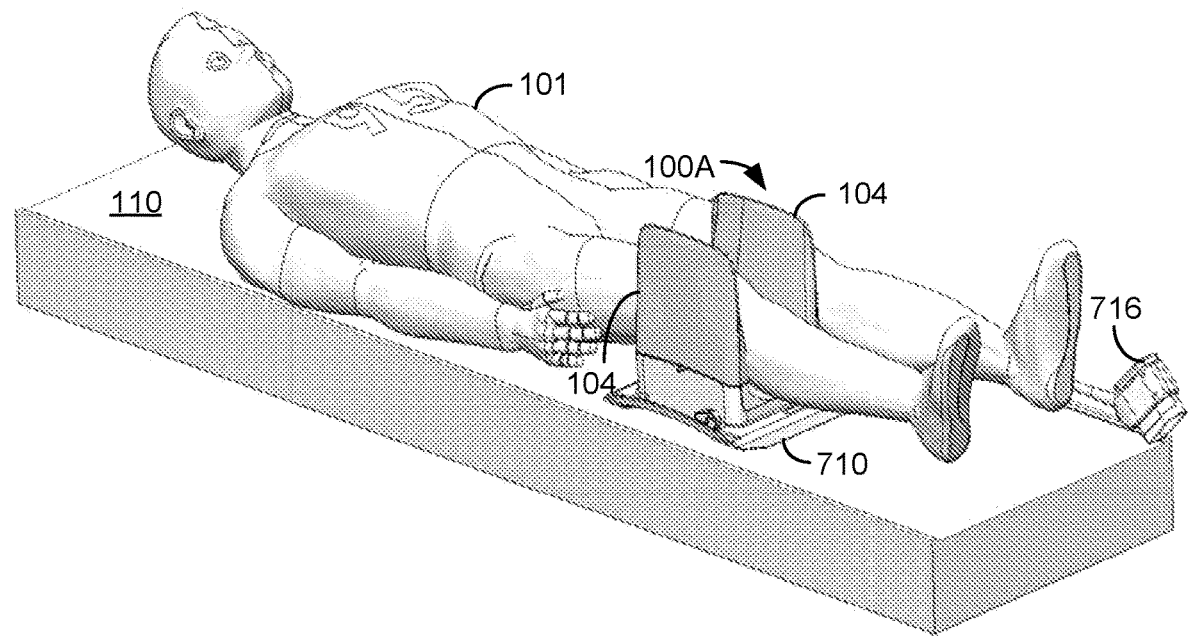
FIGS. 8A and 8B illustrate views of some embodiments of an RF surface coil for scanning a knee anatomy, placed on a patient table and configured to scan the right knee.
Figure 8B:
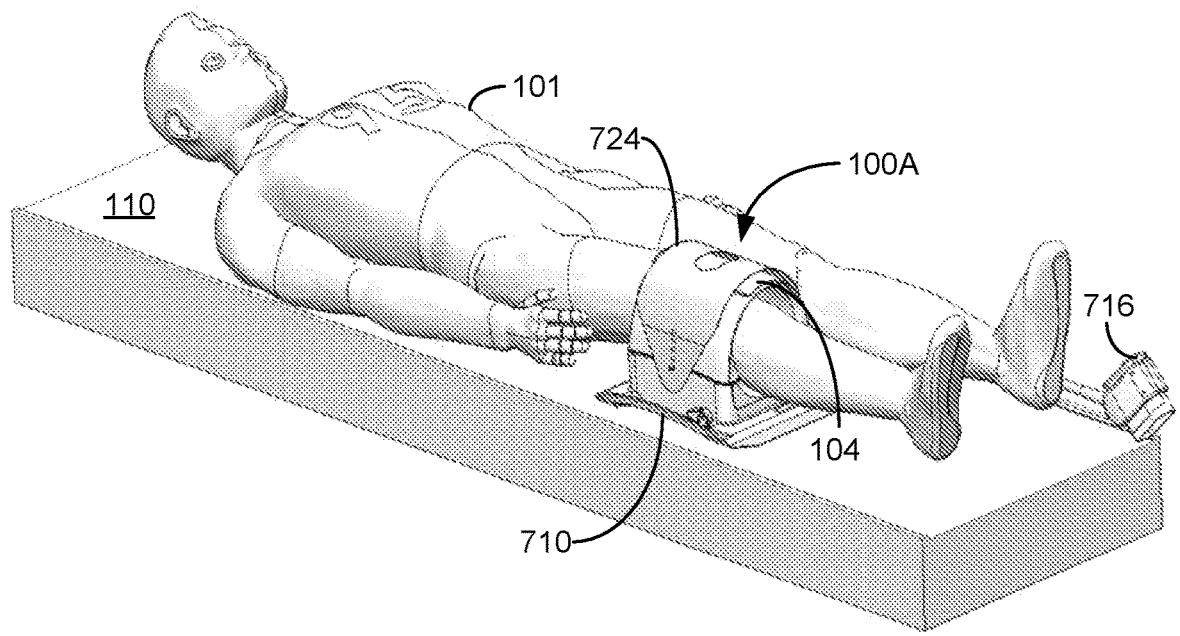

FIGS. 8A and 8B illustrate views of some embodiments of the RF surface coil 100A for scanning a knee anatomy, placed on a patient table 110 and configured to scan the right knee of a patient 101. More specifically, FIG. 8A depicts the RF surface coil 100A in an open configuration in which the two flexible upper members 104 are spread apart so that the knee of the patient 101 may be placed atop the rigid lower member 102. FIG. 8A illustrates the RF surface coil 100A in a closed configuration in which the two flexible upper members 104 are positioned more closely to the knee to be imaged. Also shown in FIG. 8B is a restraint (e.g., a flexible strap 724) that may be attached at both ends thereof to the rigid lower member 102 to maintain the position of the flexible upper members 104 during imaging.

Figure 9:
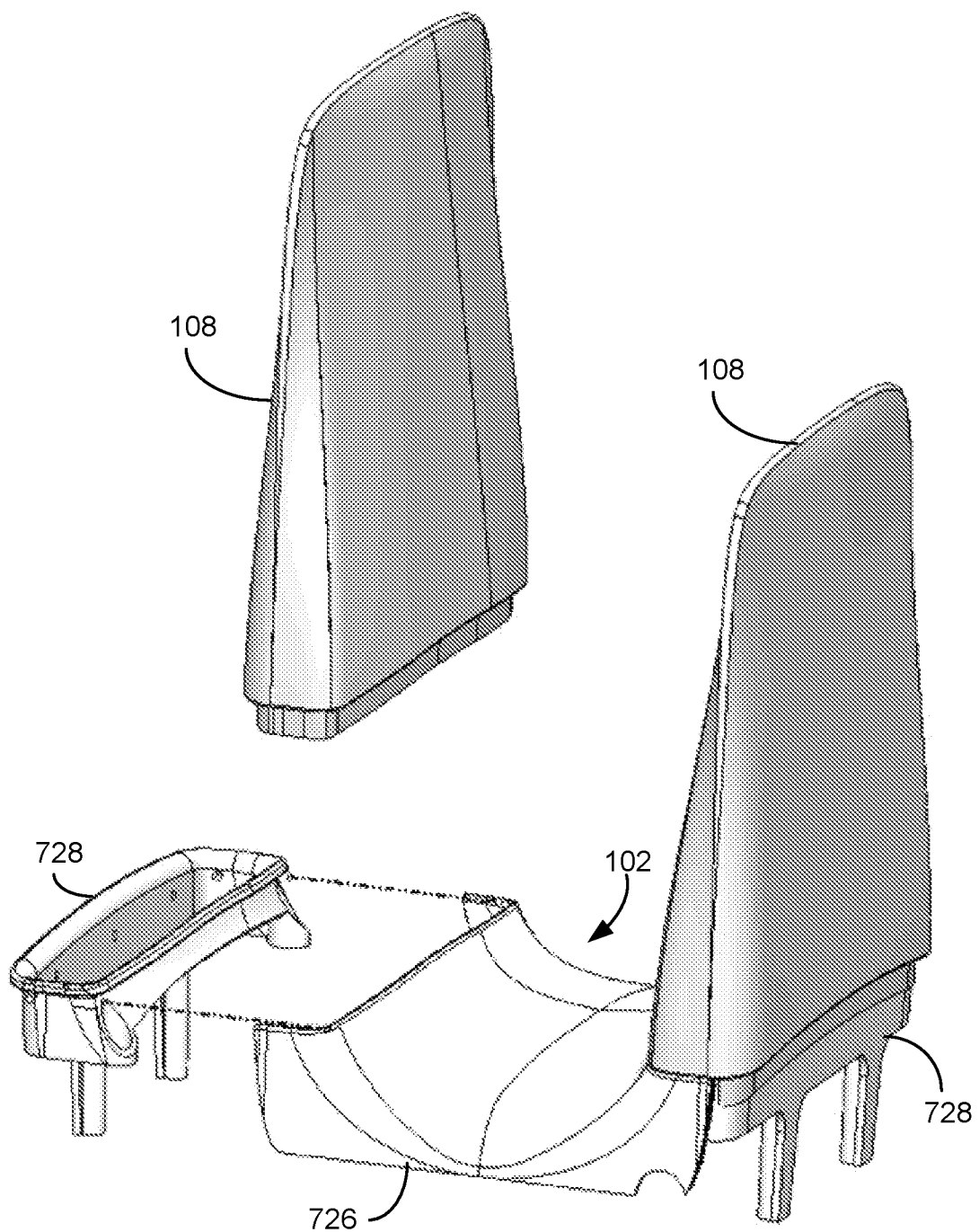
FIGS. 9-11 illustrate views of some embodiments of an assembly of an outer layer of an RF surface coil for scanning a knee anatomy, with an internal bracket used to press the outer layer against an interior surface of an outer enclosure.
Figure 10:
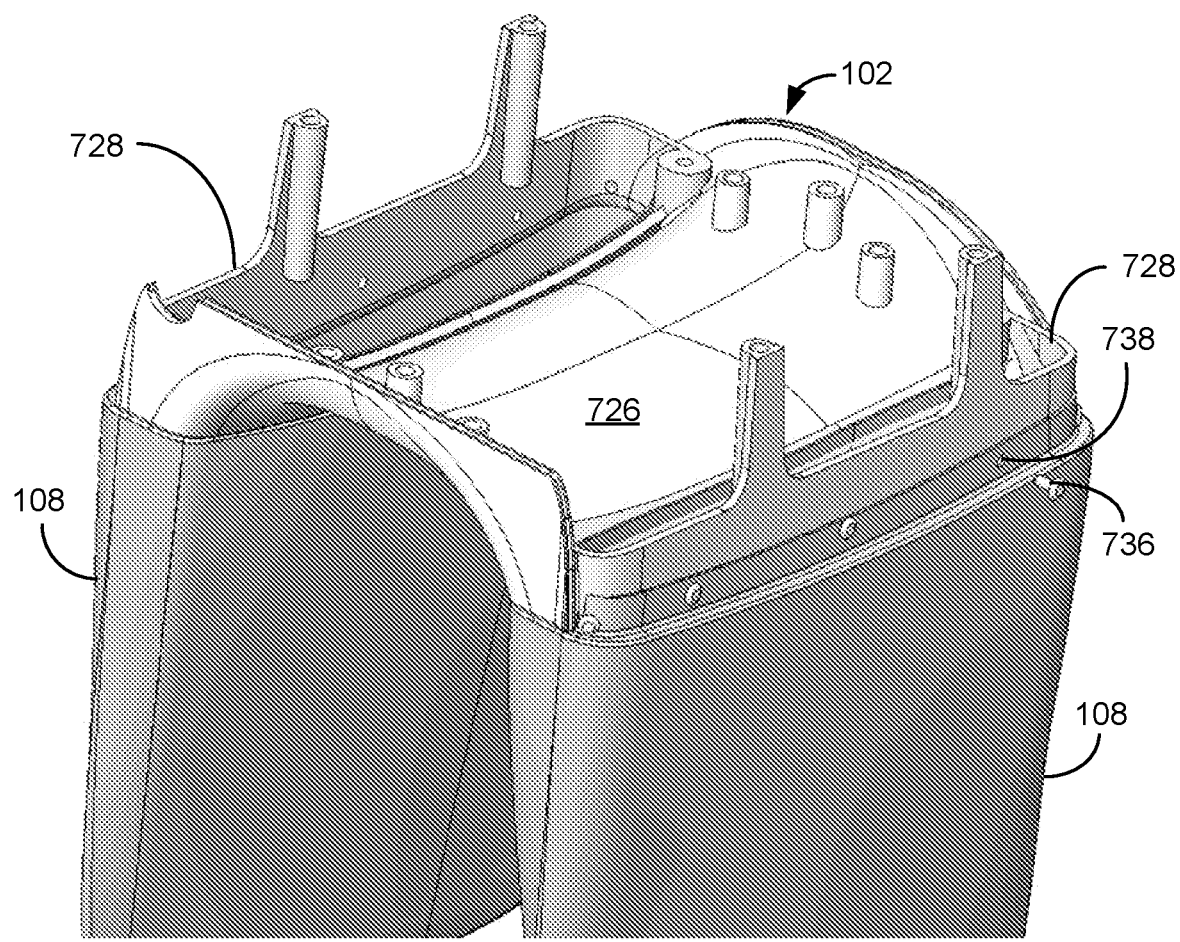
Figure 11:
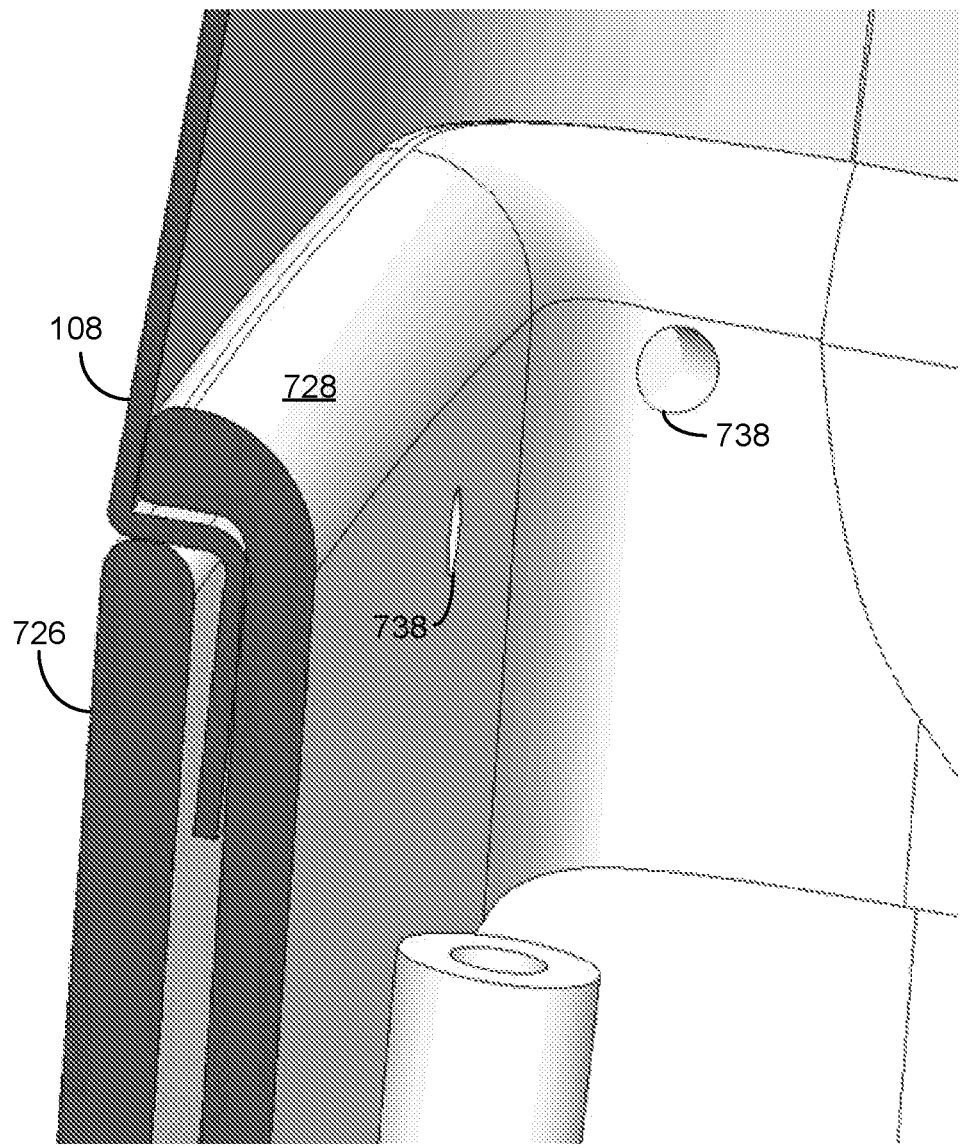

FIGS. 9-11 illustrate some embodiments of an assembly of an outer layer 108 of FIG. 1 (e.g., an exterior fabric cover, which is shown as the visible portion of the flexible upper members 104) of the RF surface coil 100A for scanning the knee anatomy, with an internal bracket 728 used to press the outer layer 108 against an interior surface of an outer enclosure 726 of the rigid lower member 102. More specifically, FIG. 9 illustrates a partially exploded view of some embodiments of the assembly. FIG. 10 illustrates a view of some embodiments of an underside of the outer enclosure 726 with the outer layers 108 and internal brackets 728 attached thereto. FIG. 11 illustrates a cross-sectional view of some embodiments of the assembled outer enclosure 726, outer layer 108, and internal bracket 728, where the internal bracket 728 is used to hold the outer layer 108 along an interior surface of the outer enclosure 726, which facilitates inhibition of the ingress of fluids.

In some embodiments, for each flexible upper member 104, the opening of the corresponding outer layer 108 may be slid over a top opening of the internal bracket 728. At that point, in some embodiments, a plurality of holes 738 about the opening of the outer layer 108 may align with corresponding holes of the internal bracket 728 such that corresponding rivets 736 or other fasteners may secure the outer layer 108 to the internal bracket 728. Thereafter, the internal bracket 728 may be pressed against a mating surface of the outer enclosure 726 and secured thereto. Additionally, an exterior component (not shown in FIGS. 9-11) may be attached to an exposed portion of the internal bracket 728, thus substantially preventing the ingress of fluid into the RF surface coil 100A via the flexible upper member 104, the rigid lower member 102, or therebetween.

While the above assembly of FIGS. 9-11 is described particularly with respect to the RF surface coil 100A of FIGS. 7A-8B, similar assemblies may be applied to other RF surface coil embodiments described above and hereafter.

Figure 12A:
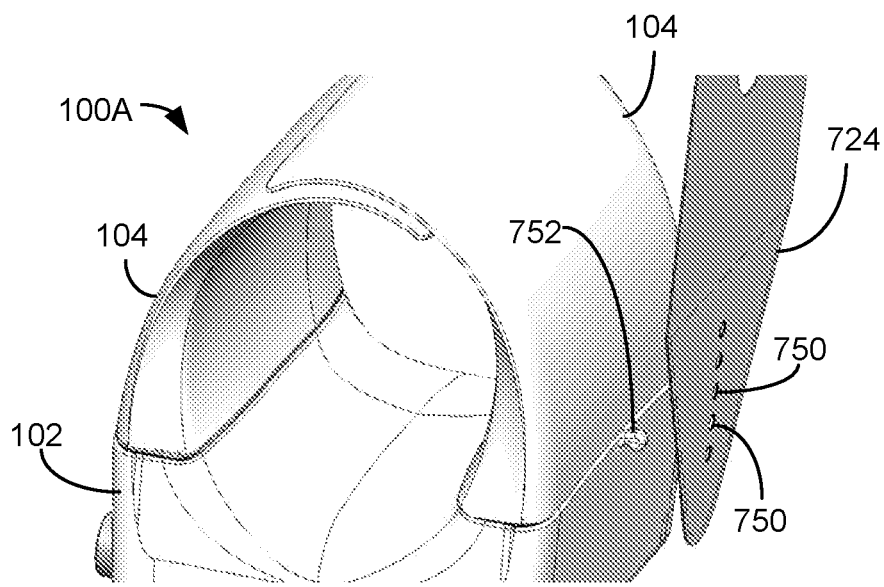
FIGS. 12A and 12B illustrate views of some embodiments of attachment of a flexible strap to an RF surface coil used for scanning a knee anatomy, where the flexible strap may be used to secure flexible members of the RF surface coil in a manner that ensures the flexible members are in close proximity to the portion of the patient's anatomy to be imaged.
Figure 12B:
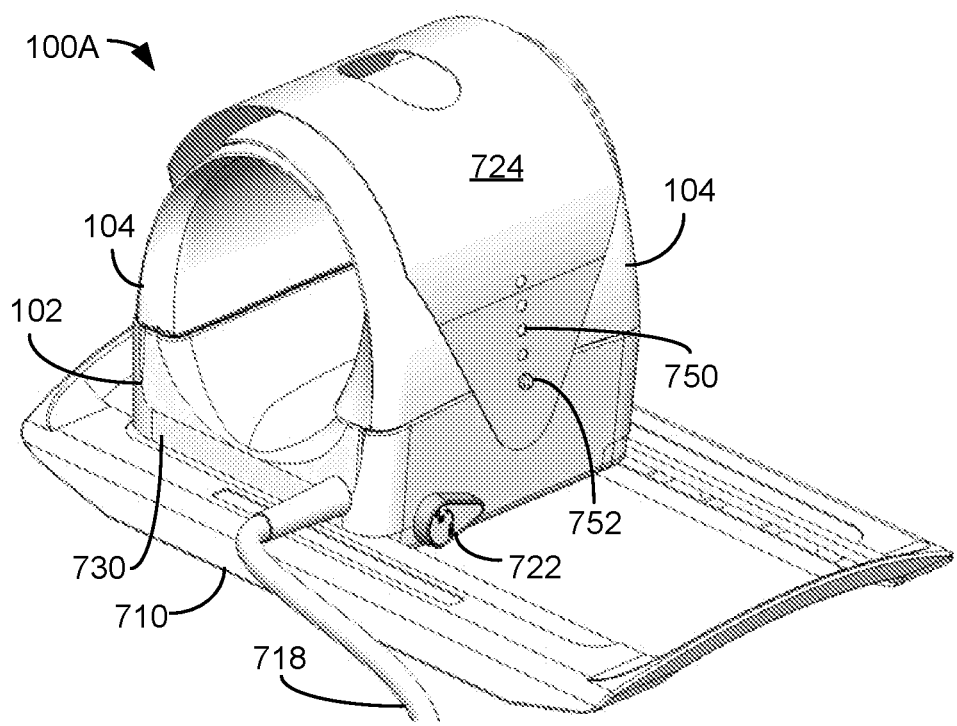

FIGS. 12A and 12B illustrate views of some embodiments of attachment of a flexible strap 724 to the RF surface coil 100A used for scanning a knee anatomy, where the flexible strap 724 may be used to secure the flexible upper members 104 in a manner that ensures the flexible upper members 104 are in close proximity to the portion of the patient's anatomy (e.g., the knee anatomy) to be imaged. In some embodiments, the flexible strap 724 may be constructed from urethane, foam, fabric, the like, or a combination thereof.

Also, in some embodiments, as illustrated in FIGS. 12A and 12B, the flexible strap 724 includes a plurality of holes 750 at either end of the flexible strap 724 for attachment to a corresponding protrusion 752 on the rigid lower member 102 of the RF surface coil 100A. As shown, the flexible strap 724 may be adjusted for proper fit and patient comfort by attaching one or both ends of the flexible strap 724 by using a particular hole 750 to attach to the protrusion 752 to provide a desired amount of tension that the flexible strap 724 applies to the flexible upper members 104 of the RF surface coil 100A and the patient anatomy to be imaged.

The use of the flexible strap 724 or similar device thus may address challenges associated with securing the patient 101 anatomy during an MRI scan to ensure the flexible RF coil elements 106 remain close to the anatomy, as well as preventing movement of the RF surface coil 100A, which may result in artifacts in the produced image. An alternative to the flexible strap 724, such as VELCRO® (manufactured by Velcro Companies) or a similar fabric-based fastening method, may serve as a reliable means to fasten a fabric strap over the lifetime of a surface coil, but may accumulate fluids and debris over time.

While the flexible strap 724 and its use is described in conjunction with the RF surface coil 100A, similar straps may be employed in connection with other RF surface coils described herein that are directed to scanning other portions of the human anatomy.

While the RF surface coil 100A of FIGS. 7A-12B is particularly configured for scanning a knee anatomy of a patient, other types of RF surface coils configured for other portions of the patient anatomy may be fashioned using a similar configuration. For example, FIGS. 13A-16B illustrate views of some embodiments of an RF surface coil 100B with a flexible RF coil element array for scanning a foot and ankle anatomy. In some embodiments, the RF surface coil 100B may include two flexible upper members 104 and a rigid lower member 102 that incorporate one or more RF coil elements, as described above in conjunction with RF surface coil 100A. Coupled to the one or more RF coil elements by way of the rigid lower member 102 may be a system cable 718 and attached system cable connector 716. Also included may be a baseframe 710 for attaching the rigid lower member 102 to a patient table.

Figure 13A:
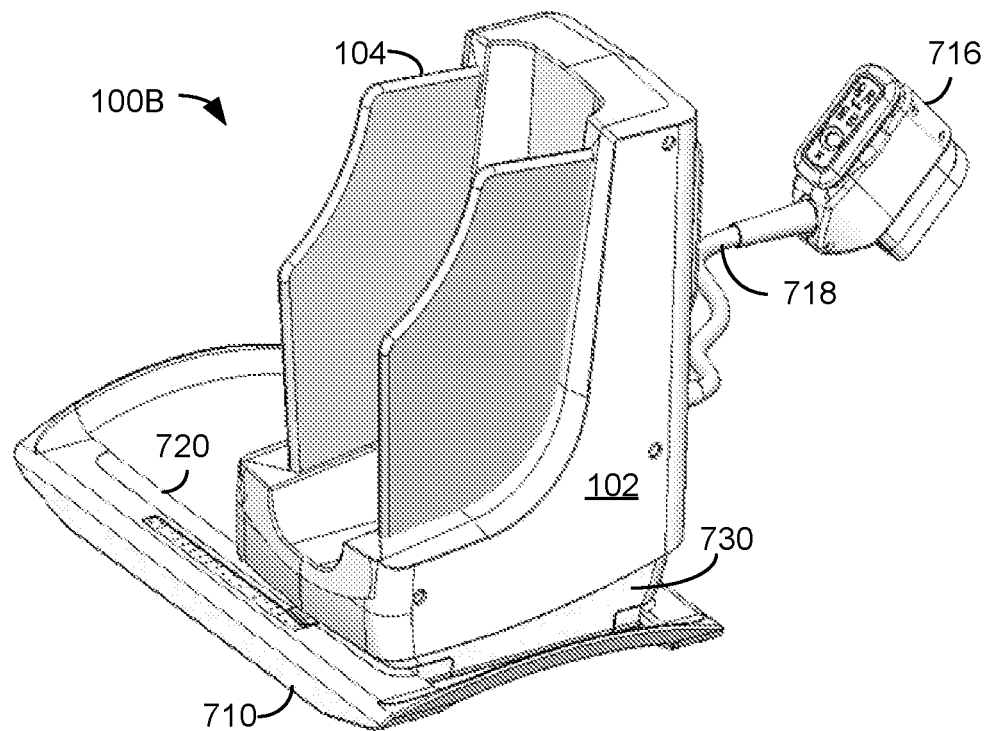
FIGS. 13A and 13B illustrate views of some embodiments of an RF surface coil for scanning a foot and ankle anatomy.
Figure 13B:
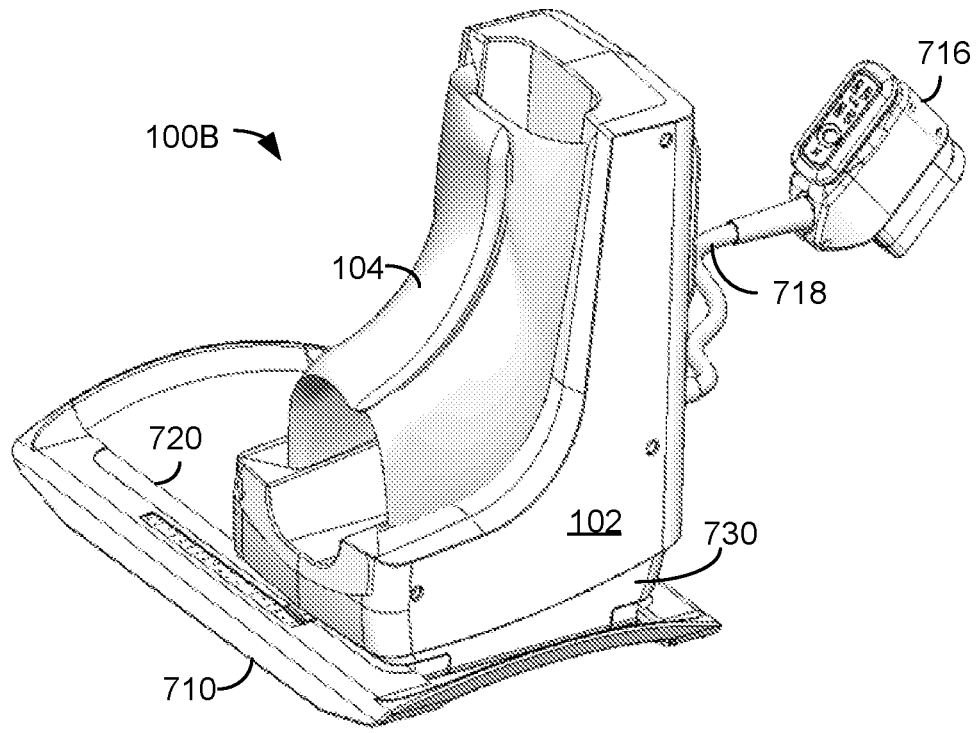

For example, FIGS. 13A and 13B illustrate views of some embodiments of an RF surface coil 100B with a flexible RF coil element array for scanning a foot and ankle anatomy (e.g., when positioned in an intermediate orientation). More specifically, FIG. 13A depicts the RF surface coil 100B when the flexible upper members 104 are in a straightened configuration to allow placement of a right foot and ankle onto the rigid lower member 102, while FIG. 13B illustrates the RF surface coil 100B when the flexible upper members 104 are in a curved (e.g., overlapped) configuration after the right foot and ankle have been positioned to place the RF coil elements in close proximity to the foot and ankle to be imaged. In some embodiments, the rigid lower member 102 is L-shaped to accommodate the approximate shape of the ankle and foot of the patient anatomy. Also, in some embodiments, the flexible upper members 104 are sized and shaped to facilitate at least some overlap of the flexible upper members 104 when folded over an ankle and foot that has been placed on the rigid lower member 102.

Figure 14A:
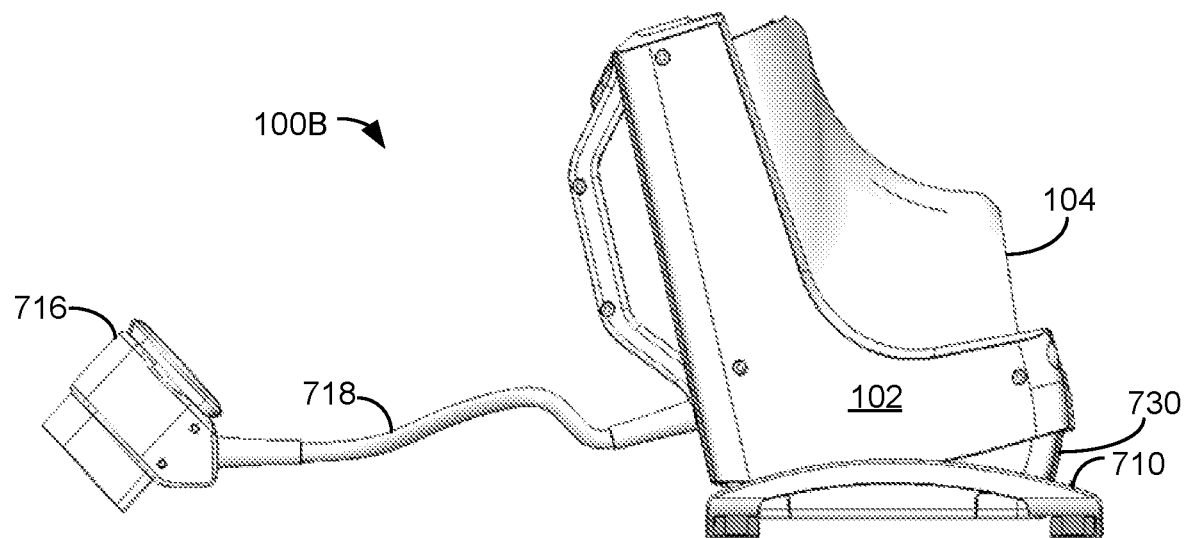
FIGS. 14A and 14B illustrate views of some embodiments of an RF surface coil for scanning a foot and ankle anatomy, positioned in two respective orientations.
Figure 14B:
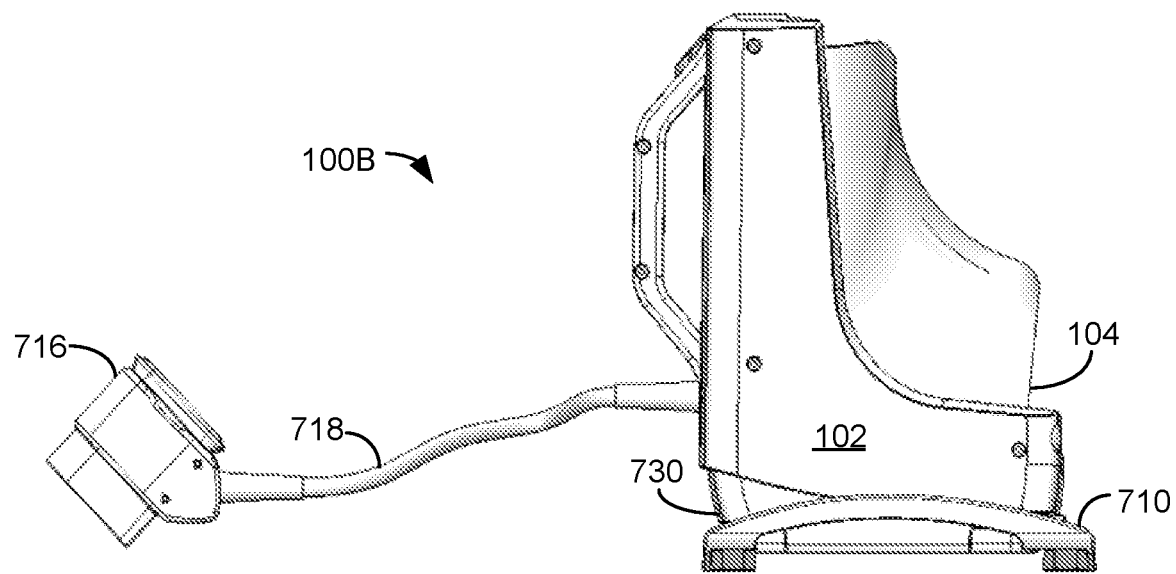

FIGS. 14A and 14B illustrate views of some embodiments of the RF surface coil 100B positioned in two additional orientations. More specifically, FIG. 14A shows the RF surface coil 100B pivoted to accommodate an ankle joint in a slightly extended position, while FIG. 14B depicts the RF surface coil 100B pivoted to accommodate an ankle joint in a slightly flexed position. To provide the various pivoted positions, the rigid lower member 102 may be configured to rotate within some range of angle about a horizontal axis (e.g., parallel to a top surface of the baseframe 710) relative to the coil-positioning structure 730. In some embodiments, the rotational orientation of the rigid lower member 102 may be locked in a number of positions relative to the coil-positioning structure 730. Depending on factors such as the size of the patient anatomy, as well as the scanning sequence used to obtain the necessary signal from the anatomy to create the image, one of the mechanical positions may result in a higher SNR of the image, resulting in higher image quality.

Figure 15A:
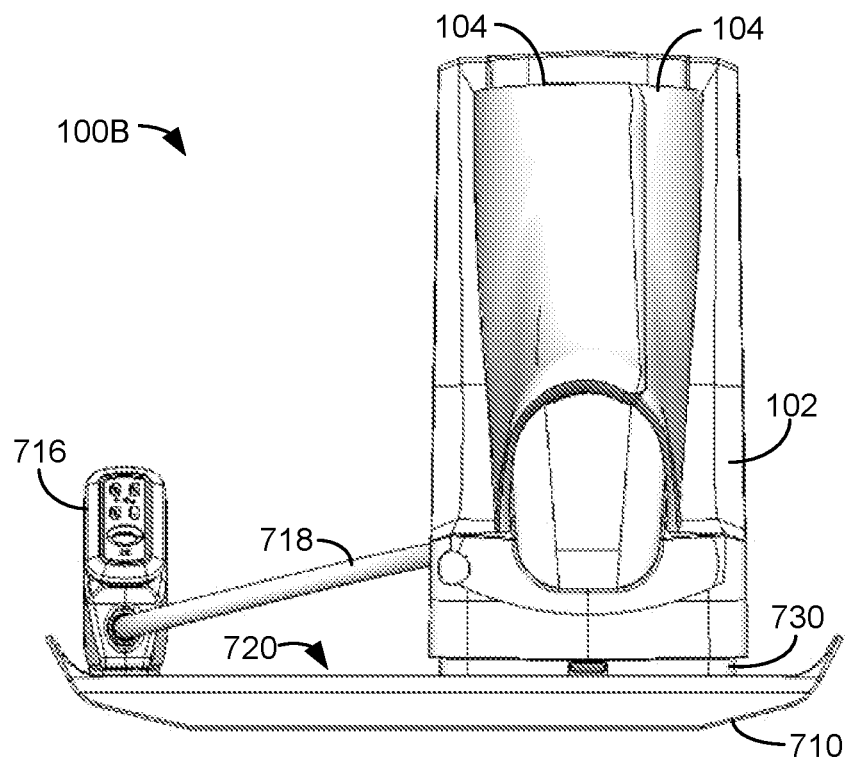
FIGS. 15A and 15B illustrate views of some embodiments of an RF surface coil for scanning a foot and ankle anatomy, configured to scan a patient's right and left foot and ankle, respectively.
Figure 15B:
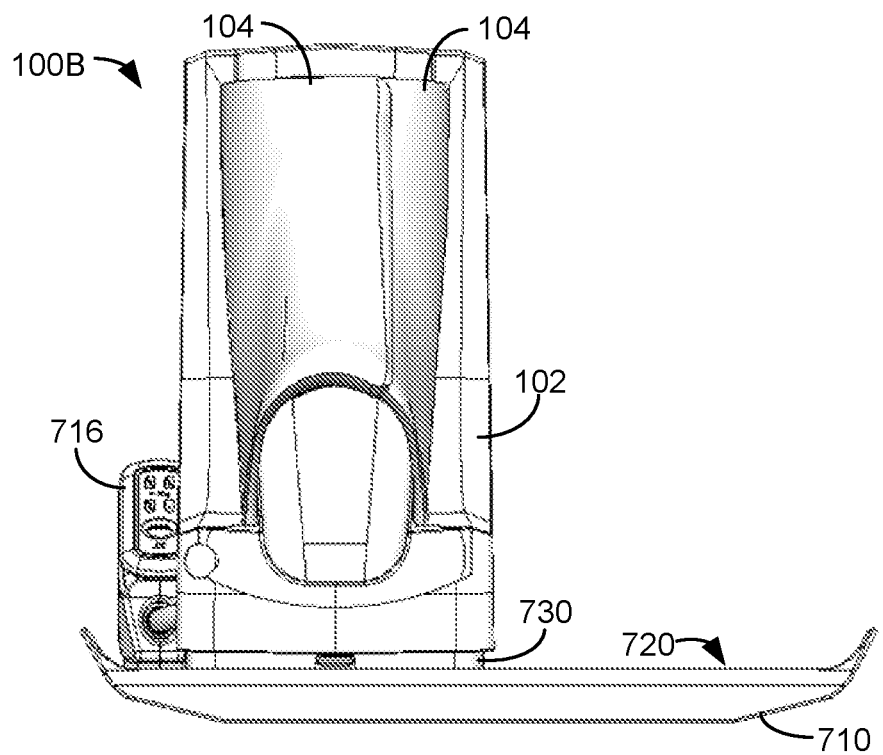
Figure 16A:
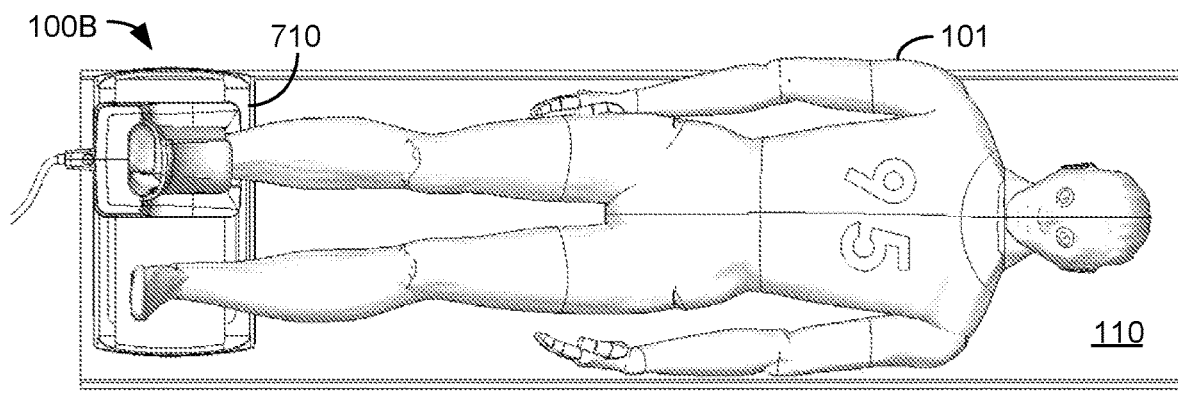
FIGS. 16A and 16B illustrate views of some embodiments of an RF surface coil for scanning a foot and ankle anatomy, placed on a patient table and configured to scan the right foot and ankle.
Figure 16B:
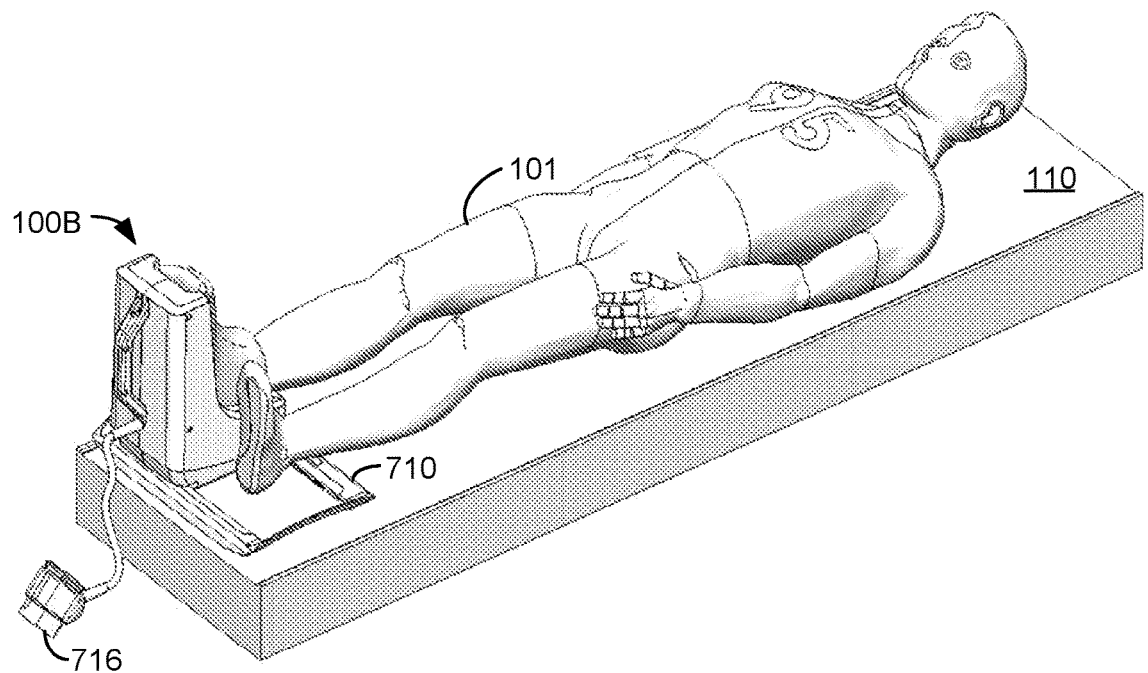

FIGS. 15A and 15B illustrate views of some embodiments of the RF surface coil 100B configured to scan a patient's right and left foot and ankle, respectively. More specifically, the coil-positioning structure 730 may slide horizontally relative to the baseframe 710 (e.g., via rails 720) and locked into position in a manner similar to that described above in conjunction with RF surface coil 100A. Corresponding to the configuration of FIG. 15A, FIGS. 16A and 16B illustrate views of some embodiments of the RF surface coil 100B when placed on the patient table 110 and configured to scan the right foot and ankle of the patient 101.

FIGS. 17A-20B illustrate views of some embodiments of the RF surface coil 100C for scanning a hand and wrist anatomy. Similar to RF surface coils 100A and 100B, the RF surface coil 100C may include two flexible upper members 104 and a rigid lower member 102 that contain one or more RF coil elements for imaging the hand and wrist anatomy. In a manner corresponding to the RF surface coils 100A and 100B, the RF surface coil 100C may provide a flexible RF coil element array with the flexible upper members 104 configured as flaps that may be flexed into a form that is optimal for scanning the hand and wrist of a patient.

In some embodiments, the rigid lower member 102 may include recesses 942 for tabs that latch the coil onto a coil-positioning structure 730 of a baseframe 710. The latching tabs thus may be configured to mount the RF surface coil 100C in multiple orientations relative to the MRI system, such as horizontally and vertically. Additionally, the coil-positioning features of the baseframe 710 may permit the rigid lower member 102 to be rotated with respect to the coronal plane of a patient and locked in a selected one of a plurality of rotated positions to improve patient comfort when the coil is oriented horizontally.

More specifically, the RF surface coil 100C may include a coil-positioning structure 730 that interfaces with the baseframe 710 (e.g. by way of rails 720 and a knob or lever 722 mechanism, shown with the knob or lever removed) to facilitate translational positioning of the rigid lower member 102 relative to the baseframe 710. The RF surface coil 100C may further include a system cable 718 coupled to the one or more RF coil elements via the rigid lower member 102 and connected to a system cable connector 716, in a manner similar to that discussed above in conjunction with RF surface coils 100A and 100B.

Figure 17A:
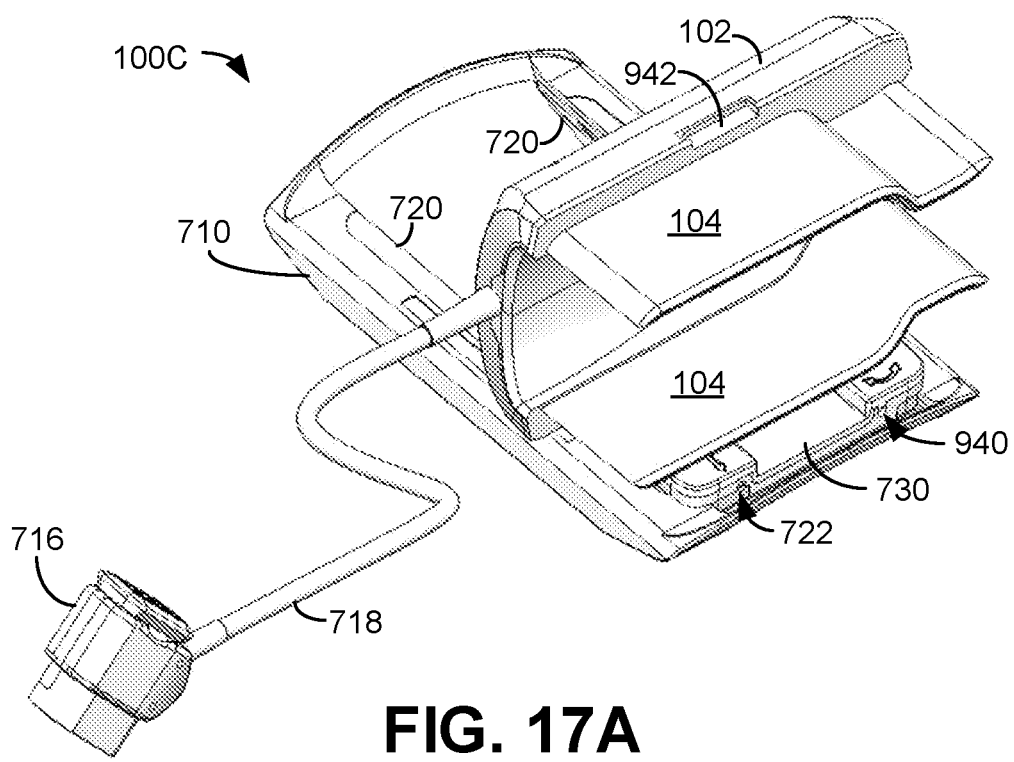
FIGS. 17A and 17B illustrate views of some embodiments of an RF surface coil for scanning a hand and wrist anatomy, configured in a vertical position.
Figure 17B:
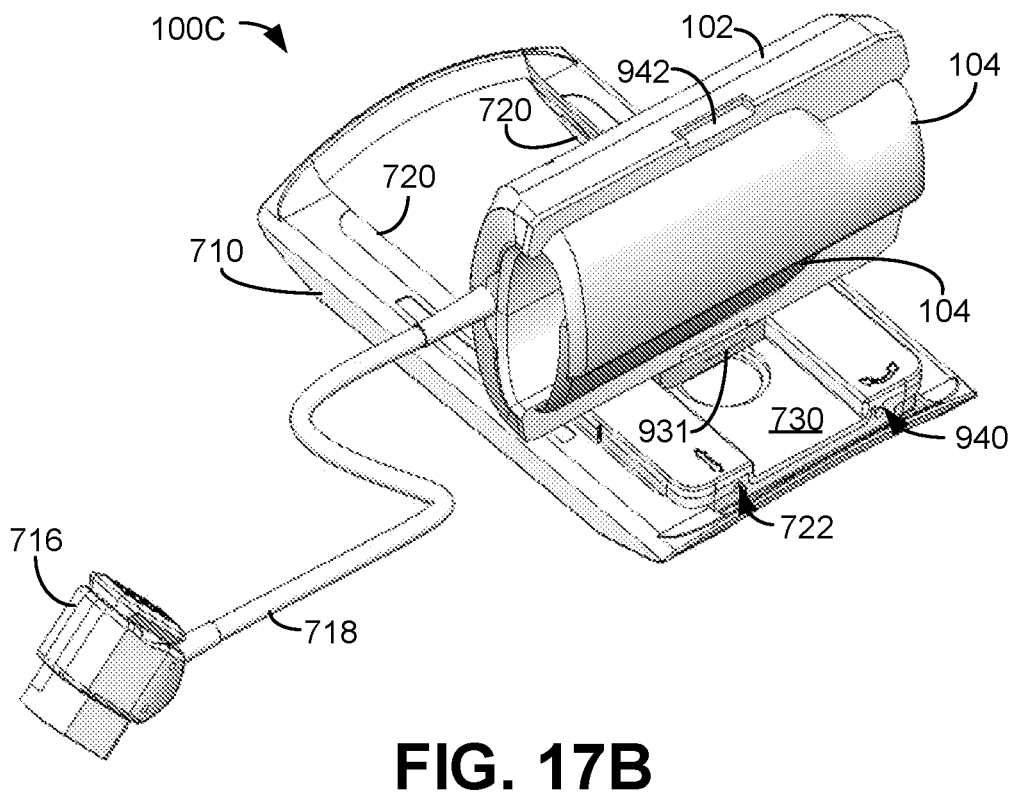

FIGS. 17A and 17B depict the RF surface coil 100C for scanning a hand and wrist anatomy, in which the rigid lower member 102 is positioned at one end of the baseframe 710. As shown, the RF surface coil 100C is configured in a position in which the left wrist and hand of a patient is vertically oriented. To facilitate this configuration, an intermediate coupler 931 may releasably or detachably couple to the rigid lower member 102. In some embodiments, the rigid lower member 102 may be coupled at an opposing side to the intermediate coupler 931 to facilitate flipping of the rigid lower member 102 relative to the baseframe 710. In some embodiments, the rigid lower member 102 is shaped to accommodate a wrist and a relatively larger hand of the patient anatomy. Also, in some embodiments, the flexible upper members 104 are sized and shaped to facilitate at least some overlap of the flexible upper members 104 when folded over the wrist and hand that has been placed on or adjacent to the rigid lower member 102.

Figure 18A:
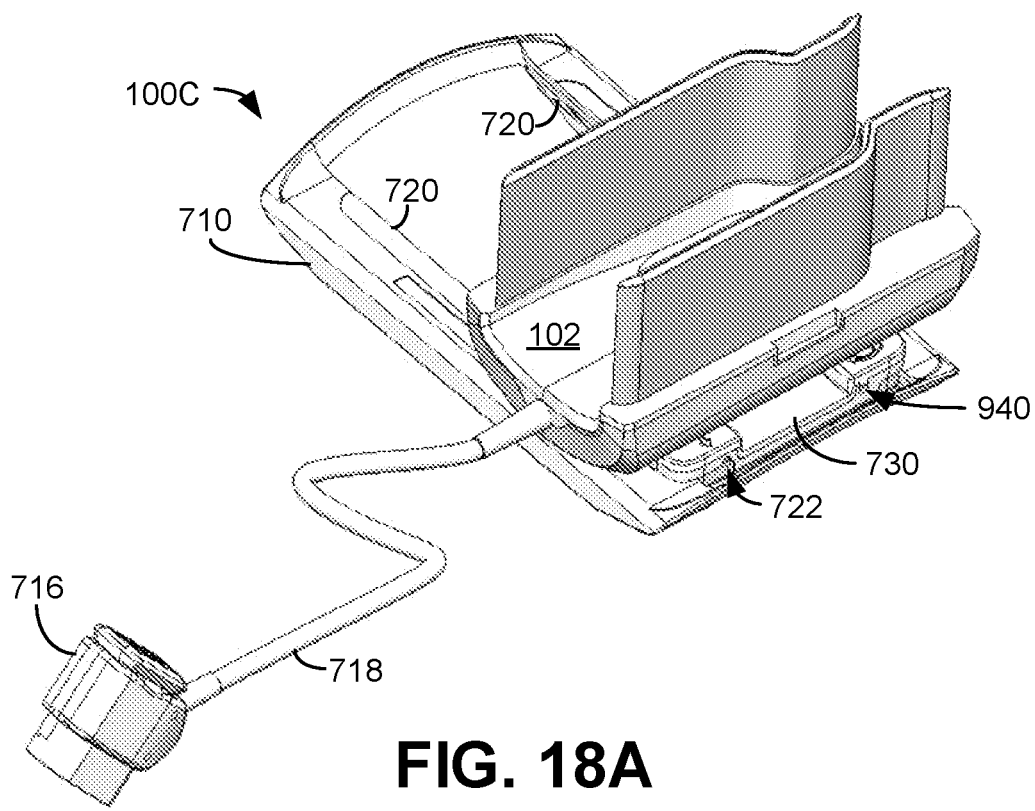
FIGS. 18A and 18B illustrate views of some embodiments of an RF surface coil for scanning a hand and wrist anatomy, configured in a horizontal position, which may permit lateral, as well as rotational, positioning of the RF surface coil.
Figure 18B:
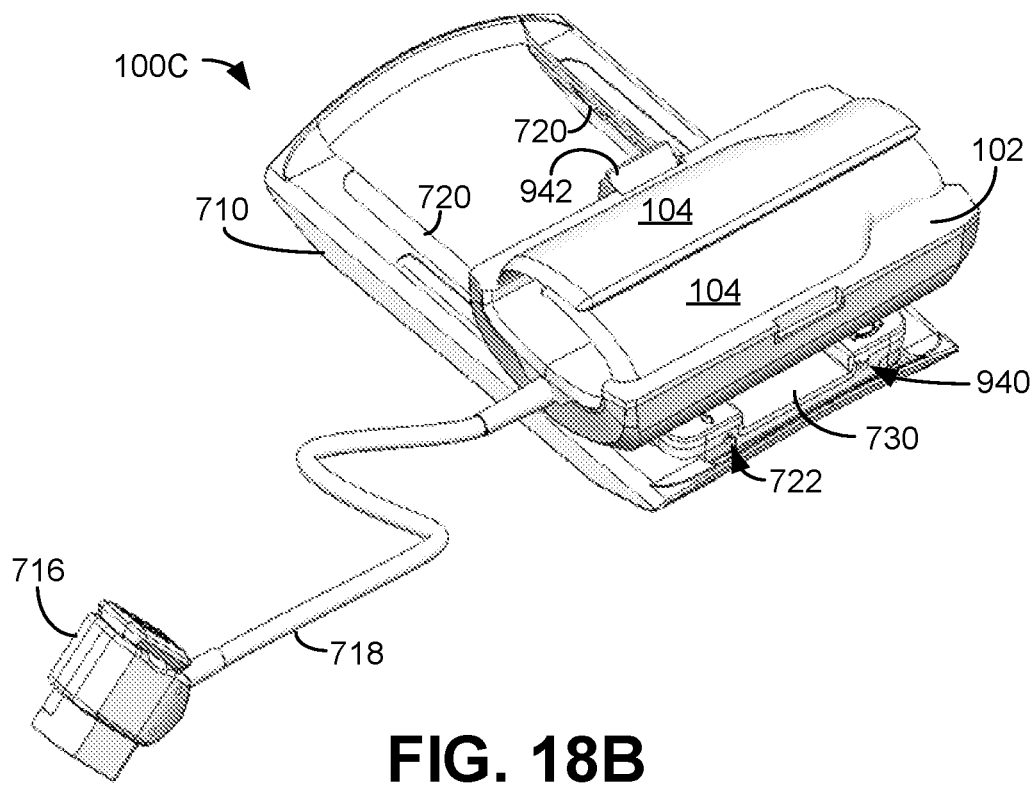

FIGS. 18A and 18B illustrate views of some embodiments of the RF surface coil 100C configured in a position in which the left wrist and hand of a patient is oriented horizontally by way of the intermediate coupler 931 (hidden from view of FIGS. 18A and 18B) releasably attached to the rigid lower member 102. In some embodiments, this horizontal configuration may also permit rotational positioning of the RF surface coil 100C about a vertical axis (e.g., normal to a top surface of the baseframe 710). More specifically, the intermediate coupler 931 may facilitate rotation and subsequent locking into a particular orientation of the rigid lower member 102 relative to the intermediate coupler 931 in some embodiments. The locking mechanism may be engaged and disengaged by way of a lever or knob mechanism 940 (indicated in FIGS. 18A and 18B with the knob or lever removed).

Figure 19A:
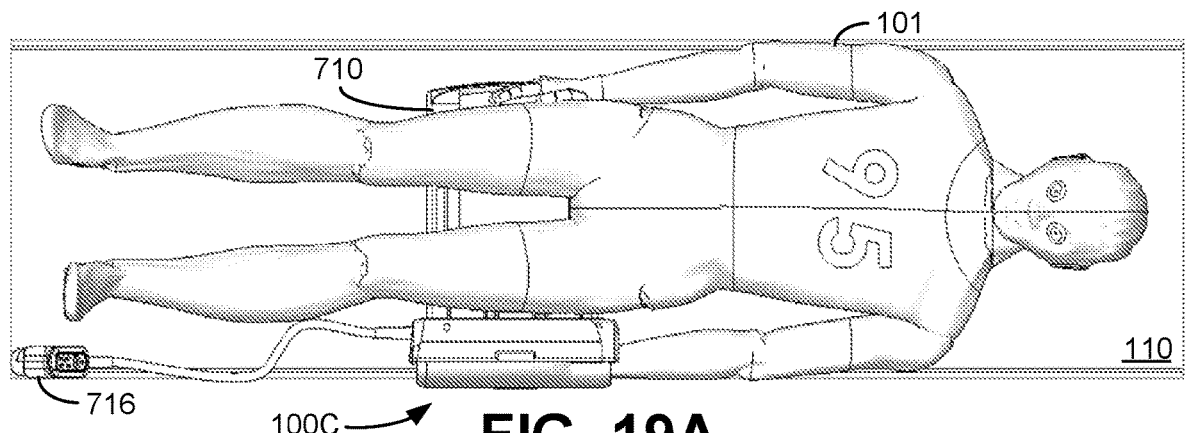
FIGS. 19A-19C illustrate views of some embodiments of an RF surface coil for scanning a hand and wrist anatomy, placed on a patient table and configured to scan the left hand and wrist anatomy in a vertical position.
Figure 19B:
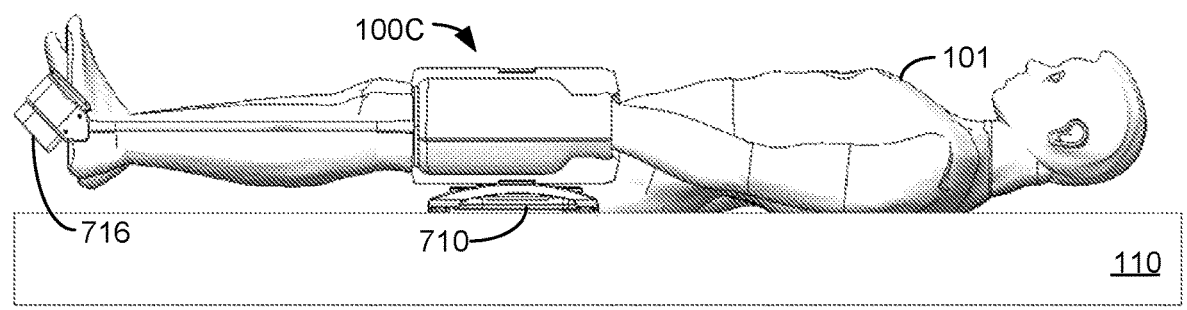
Figure 19C:
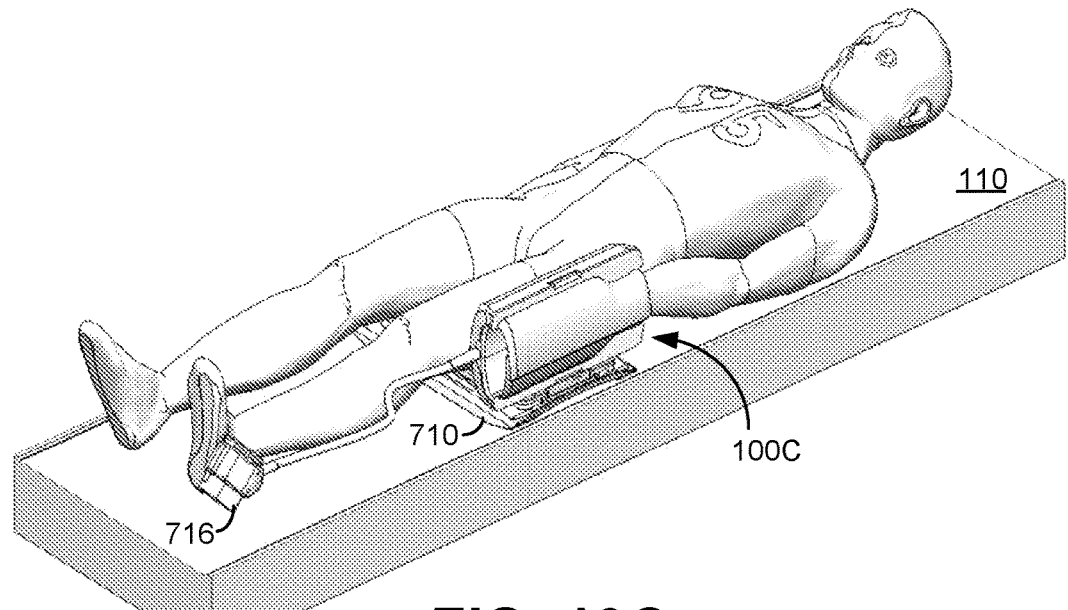
Figure 20A:
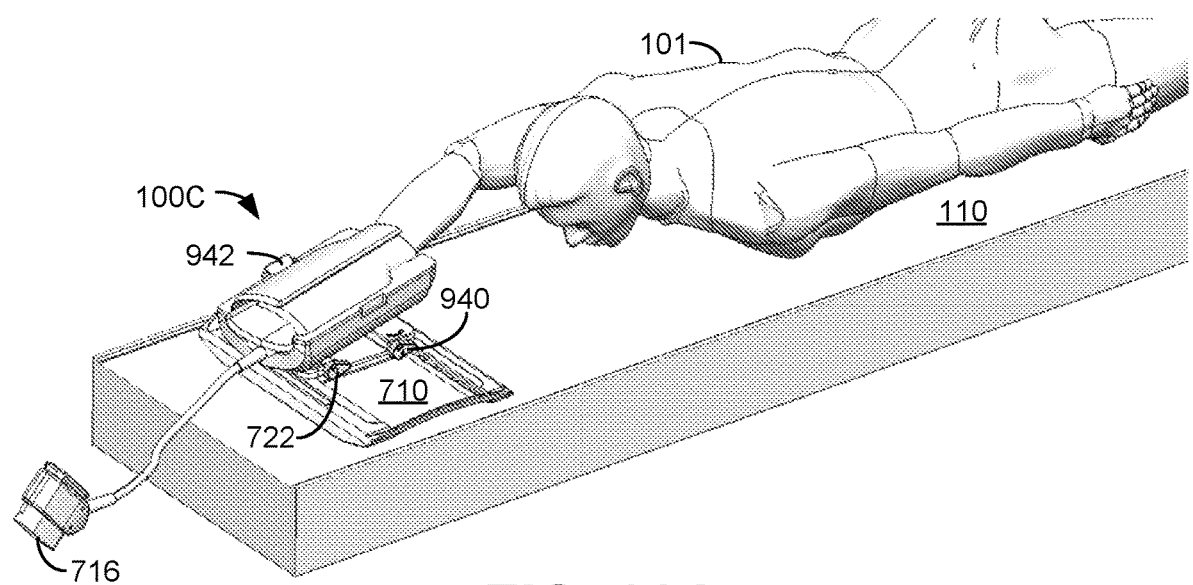
FIGS. 20A and 20B illustrate views of some embodiments of an RF surface coil for scanning a hand and wrist anatomy, placed on a patient table and configured to scan the right hand and wrist anatomy in a horizontal position.
Figure 20B:
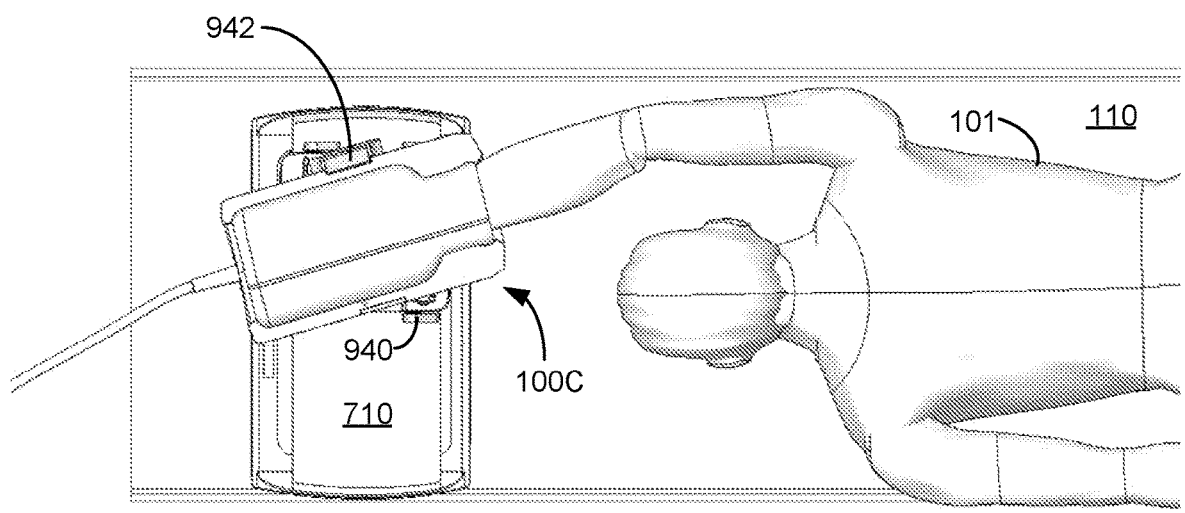

FIGS. 19A-19C illustrate views of some embodiments of the RF surface coil 100C placed on a patient table 110 and configured to scan the left hand and wrist anatomy of a patient 101 in a vertical position, as described above in conjunction with FIGS. 17A and 17B, while the patient 101 lies supine on the patient table 110. FIGS. 20A and 20B illustrate views of some embodiments of the RF surface coil 100C placed on the patient table 110 and configured to scan the right hand and wrist anatomy in a horizontal position and rotated relative to the baseframe 710, as described above in connection with FIGS. 18A and 18B, while the patient 101 lies prone on the patient table 110.

While the embodiments described above generally include two flexible upper members coupled to a rigid lower member, FIGS. 21A-26 illustrate views of some embodiments of an RF surface coil 100D for general musculoskeletal scanning, such as for imaging a shoulder, elbow, or other portion of a patient anatomy, that includes a single flexible upper member 104 coupled to a rigid lower member 102. The flexible upper member 104 and the rigid lower member 102 may include a flexible RF coil element array. In addition, the RF surface coil 100D may include a system cable 718 and associated system cable connector 716 for electrical coupling with the MRI system, where the system cable 718 may be coupled to the one or more RF coil elements via the rigid lower member 102. Further, the rigid lower member 102 may be mounted to a baseframe 710, which may be attached to a patient table. Accordingly, the patient's anatomy (e.g., shoulder) may rest on the rigid lower member 102, and the flexible upper member 104 may be wrapped around a portion of the anatomy for imaging. In some embodiments, the rigid lower member 102 may be detached from the baseframe 710 and remounted thereto in a plurality of orientations (e.g., a first orientation and a second orientation to scan either side of the patient).

Figure 21A:
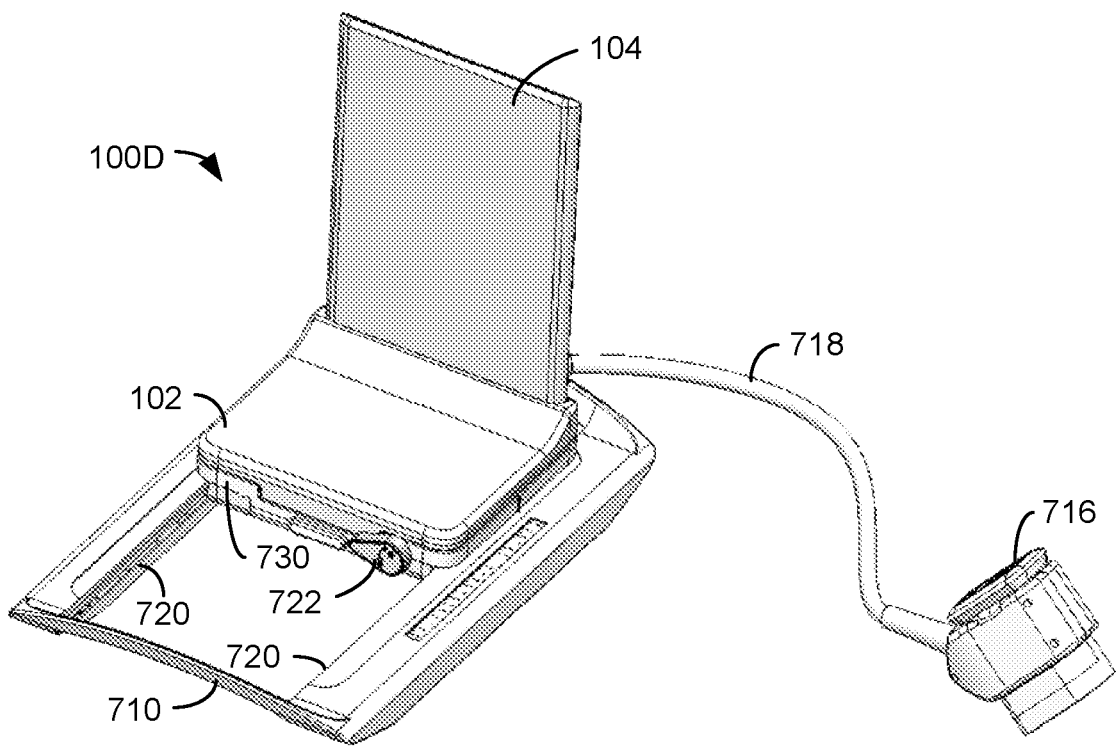
FIGS. 21A and 21B illustrate views of some embodiments of an RF surface coil for general musculoskeletal scanning in a first configuration.
Figure 21B:
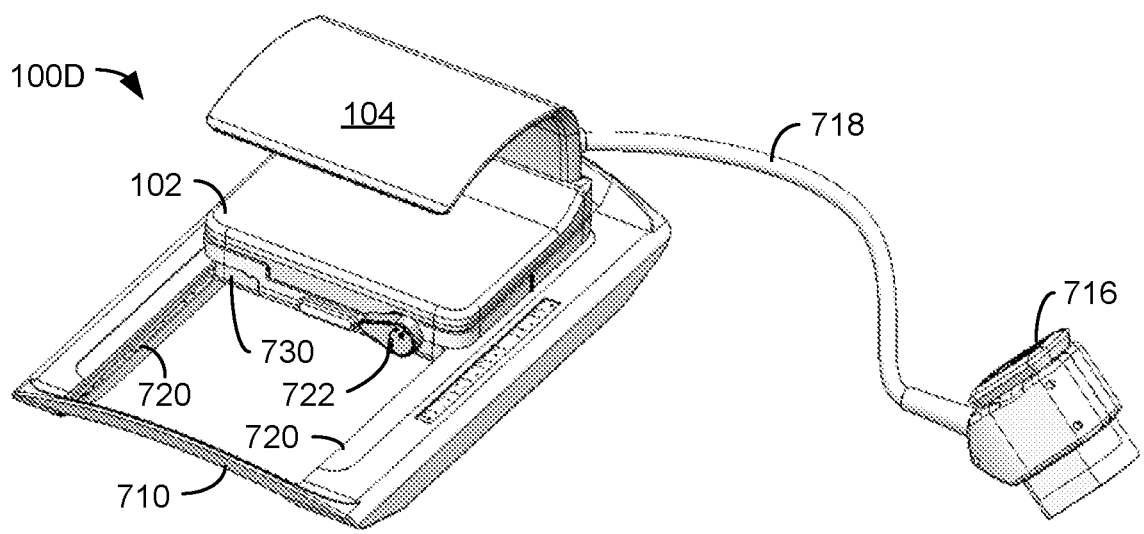

More specifically, FIGS. 21A and 21B illustrate views of some embodiments of the RF surface coil 100D in a first configuration in which the rigid lower member 102 is positioned at a first end of the baseframe 710. FIG. 21A depicts the flexible upper member 104 in a straight or flat configuration (e.g., to facilitate placement of the patient anatomy to be imaged atop the rigid lower member 102). By contrast, FIG. 21B shows the flexible upper member 104 in a curved or bent configuration (e.g., to position the one or more RF coil elements in proximity to the patient anatomy to be imaged).

As shown in connection with RF surface coils 100A, 100B, and 100C, the rigid lower member 102 of the RF surface coil 100D may be located along multiple positions of the baseframe 710 via rails 720 and a coil-positioning structure 730 coupled to the rigid lower member 102. Also, the coil-positioning structure 730 may be disengaged and reengaged by way of a knob or lever 722 to release and lock the position of the coil-positioning structure 730, and thus the rigid lower member 102, relative to the baseframe 710.

Figure 22A:
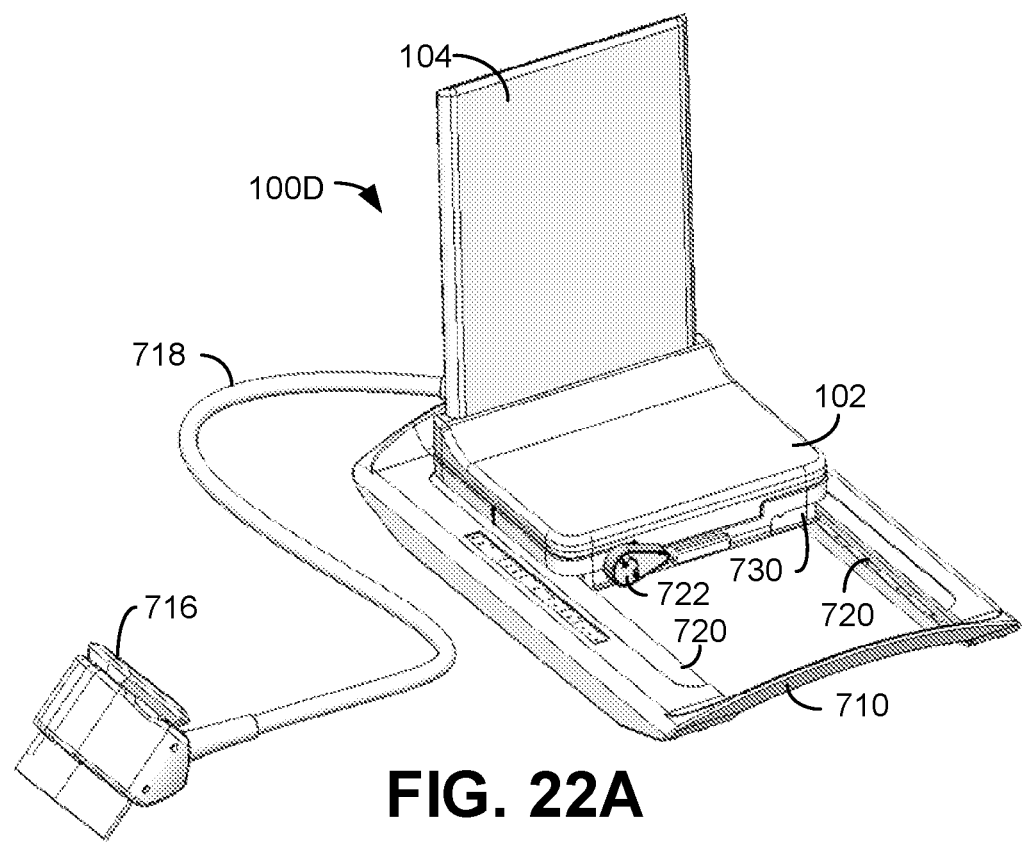
FIGS. 22A and 22B illustrate views of some embodiments of an RF surface coil for general musculoskeletal scanning in a second configuration.
Figure 22B:
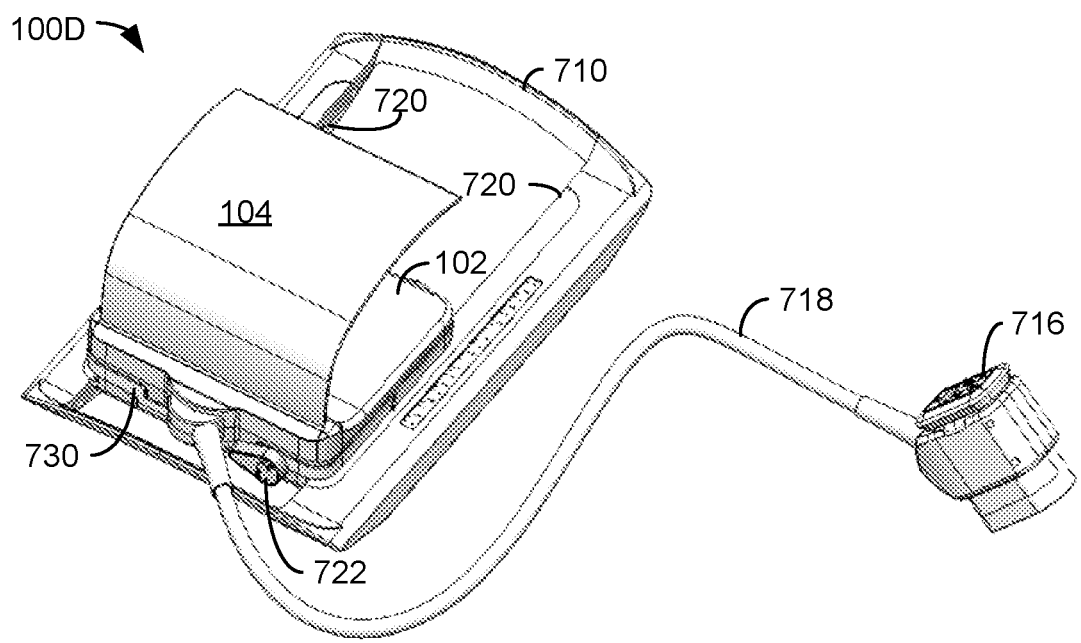

FIGS. 22A and 22B illustrate views of some embodiments of the RF surface coil 100D in a second configuration in which the rigid lower member 102 is positioned at a second end of the baseframe 710 opposite the first end (e.g., to image portions located on an opposite side of the patient anatomy from that imaged via the first configuration of FIGS. 21A and 21B). Moreover, FIG. 22A depicts the flexible upper member 104 in a straight or flat configuration, and FIG. 22B shows the flexible upper member 104 in a curved or bent configuration, in a manner similar to FIGS. 21A and 21B, discussed above.

In some embodiments, to transition between the first configuration and the second configuration, the coil-positioning structure 730 may be disengaged from baseframe 710, thus allowing the coil-positioning structure 730, the rigid lower member 102, and the flexible upper member 104 to be repositioned to the second end of the baseframe 710. The coil-positioning structure 730 thereafter may be reengaged to the baseframe 710 (e.g., via lever 722) to lock the coil-positioning structure 730 in place. In addition, the rigid lower member 102 may be detached from the coil-positioning structure 730 and rotated by some amount (e.g., 180 degrees) to facilitate imaging of a patient anatomy, such as an opposing shoulder of the patient.

Figure 23:
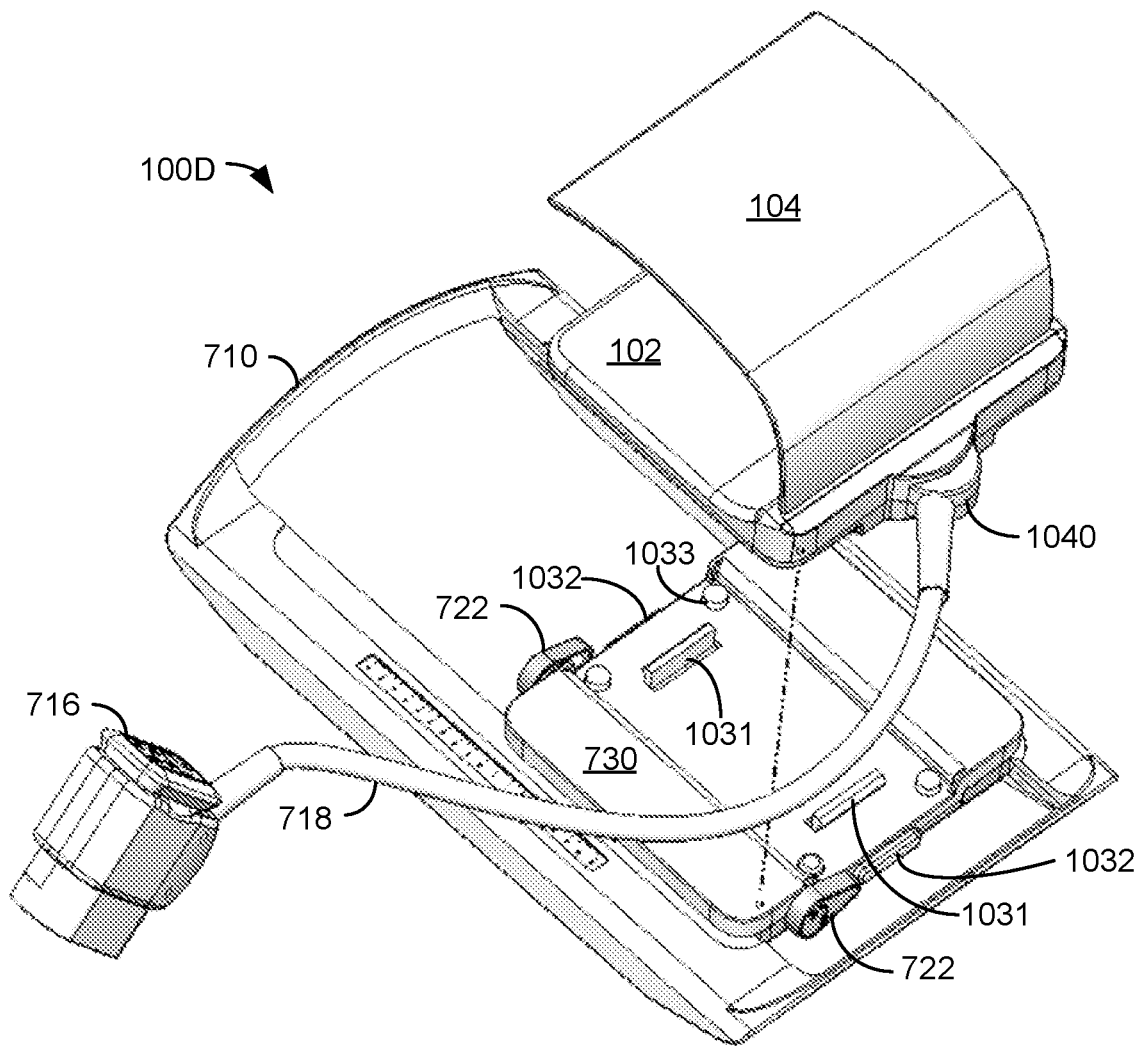
FIG. 23 illustrates a view of some embodiments of an RF surface coil for general musculoskeletal scanning while transitioning between a first configuration and a second configuration.

FIG. 23 illustrates a view of some embodiments of the RF surface coil 100D while transitioning between the first and second configurations. As shown, the rigid lower member 102 is detached from the coil-positioning structure 730. In some embodiments, in an attached configuration, recesses of the rigid lower member 102 (hidden in the view of FIG. 23) may be engaged by tabs 1031, which may be operated by pressing buttons 1032 to disengage the rigid lower member 102 from the coil-positioning structure 730. The rigid lower member 102 and the flexible upper member 104 may then be rotated and subsequently reattached to the coil-positioning structure 730 (e.g., by aligning pegs 1033 of the coil-positioning structure 730 with depressions of the rigid lower member 102 (also hidden in FIG. 23) and pressing the rigid lower member 102 downward to engage the tabs 1031 with the recesses mentioned above). The latching tabs 1031 and associated recesses may be configured to permit the rigid lower member 102 to be mounted in a plurality of orientations relative to the baseframe 710 (e.g., to scan either side of the patient).

Figure 24A:
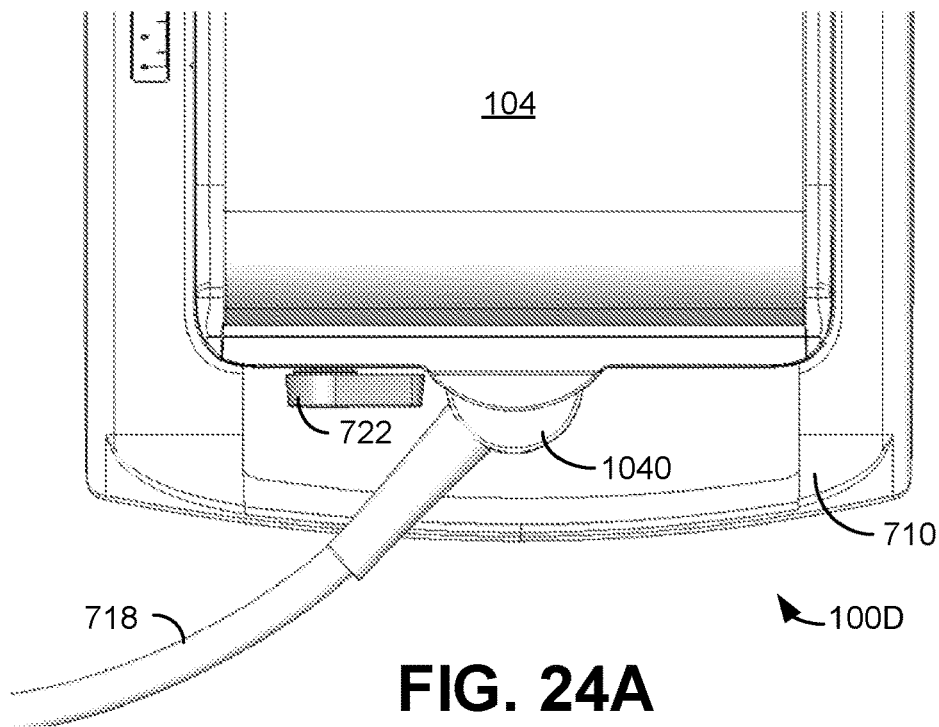
FIGS. 24A and 24B illustrate views of some embodiments of an RF surface coil for general musculoskeletal scanning, in which a system cable exit of the RF surface coil may be pivoted in a range of positions to facilitate cable routing to a location where the cable is to be connected to an MRI system.
Figure 24B:
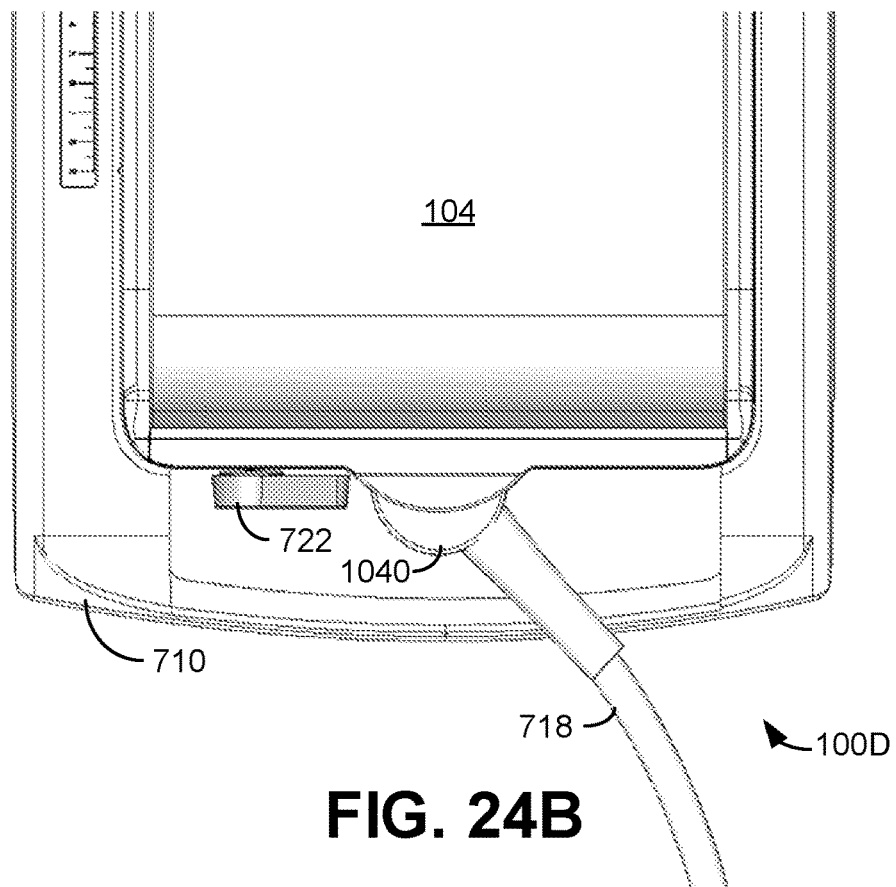

FIGS. 24A and 24B illustrate views of some embodiments of the RF surface coil 100D in which a system cable exit of the RF surface coil 100D may be pivoted within a range of positions to facilitate cable routing to a location where the system cable 718 is to be connected to an MRI system (e.g., to further facilitate transitioning between the first and second configurations). The system cable 718 may be coupled to the one or more RF coil elements by way of a pivoting housing 1040 at the exit of the system cable 718 from the rigid lower member 102. In some embodiments, the pivoting housing 1040 may facilitate a compact bend radius of the system cable 718, which may alleviate stresses in the system cable 718 in the vicinity of the rigid lower member 102 when being routed toward the connection to the MRI system via the system cable connector 716. In some embodiments, FIG. 24A corresponds with the first configuration depicted in FIGS. 21A and 21B, and FIG. 24B is associated with the second configuration illustrated in FIGS. 22A and 22B.

While several structural features (e.g., the single flexible upper member 104, the rigid lower member 102, and the pivoting housing 1040) are described above in connection with RF surface coil 100D, other RF surface coils (e.g., RF surface coils 100A, 100B, and 100C) discussed herein may also benefit from the inclusion of such features.

Figure 25A:
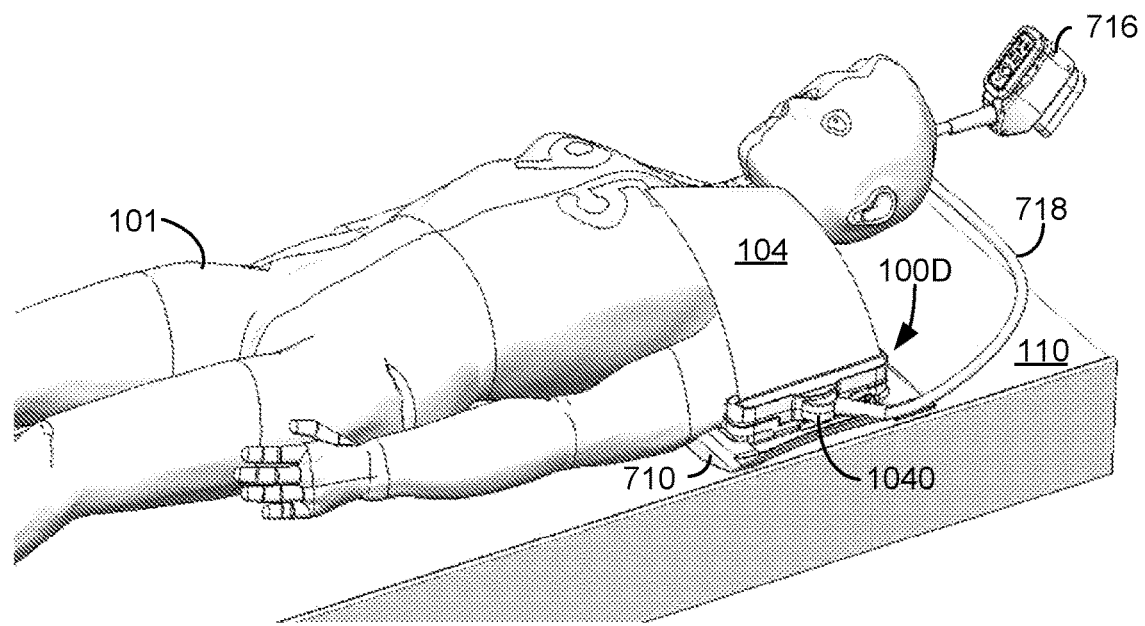
FIGS. 25A-25C illustrate views of some embodiments of an RF surface coil for general musculoskeletal scanning, placed on a patient table and configured to scan a left shoulder anatomy.
Figure 25B:
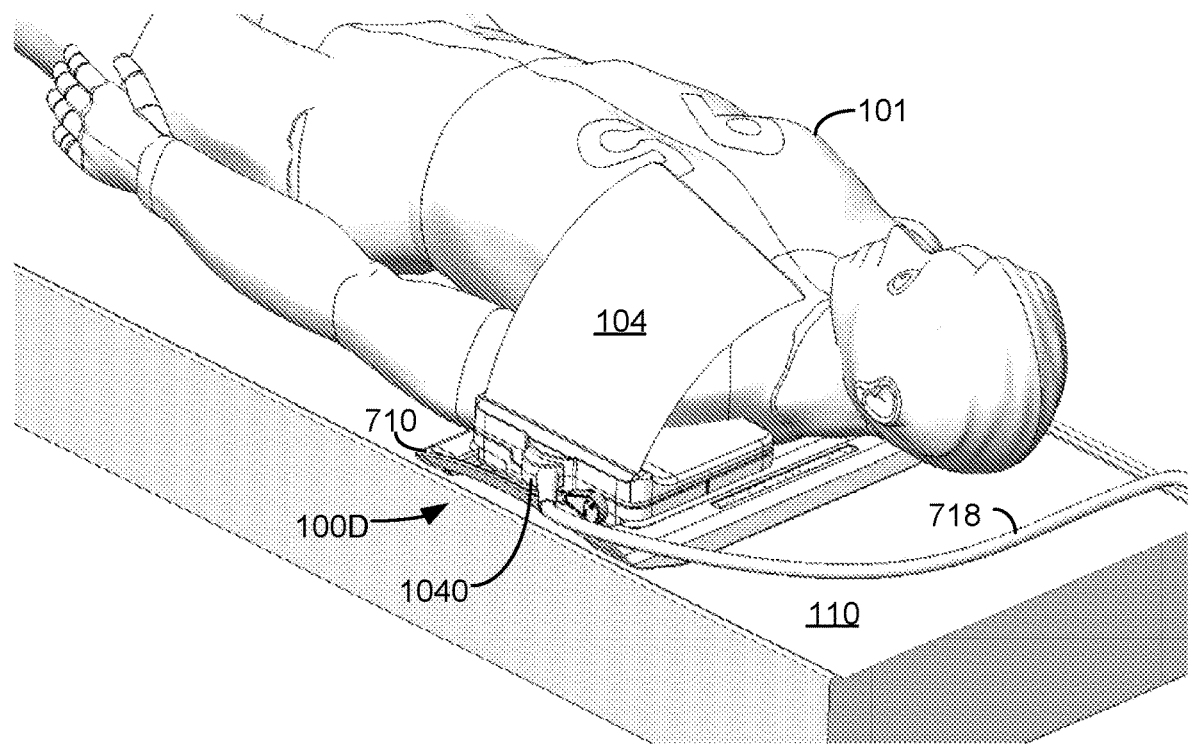
Figure 25C:
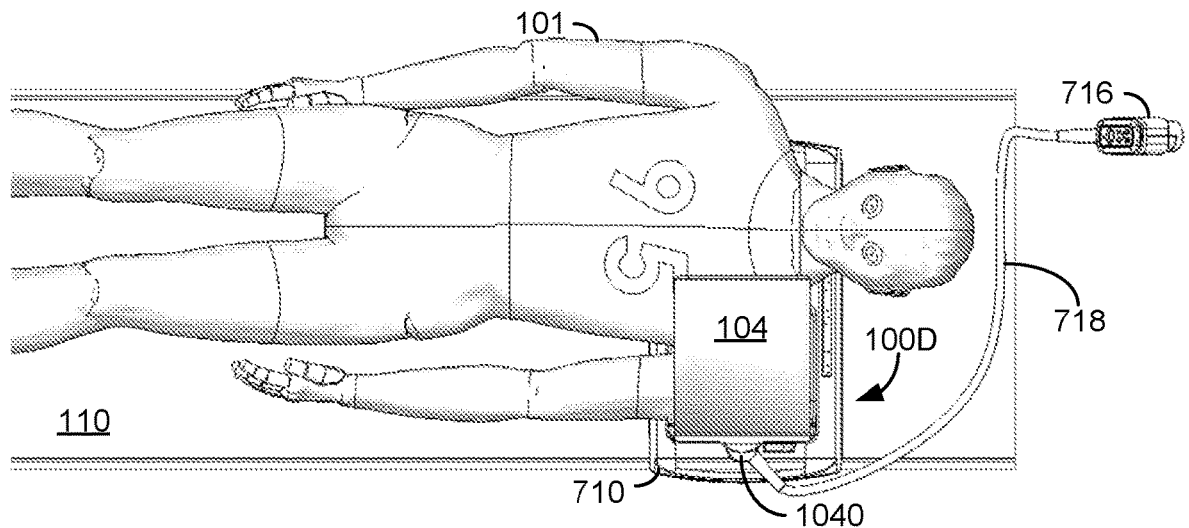
Figure 26A:
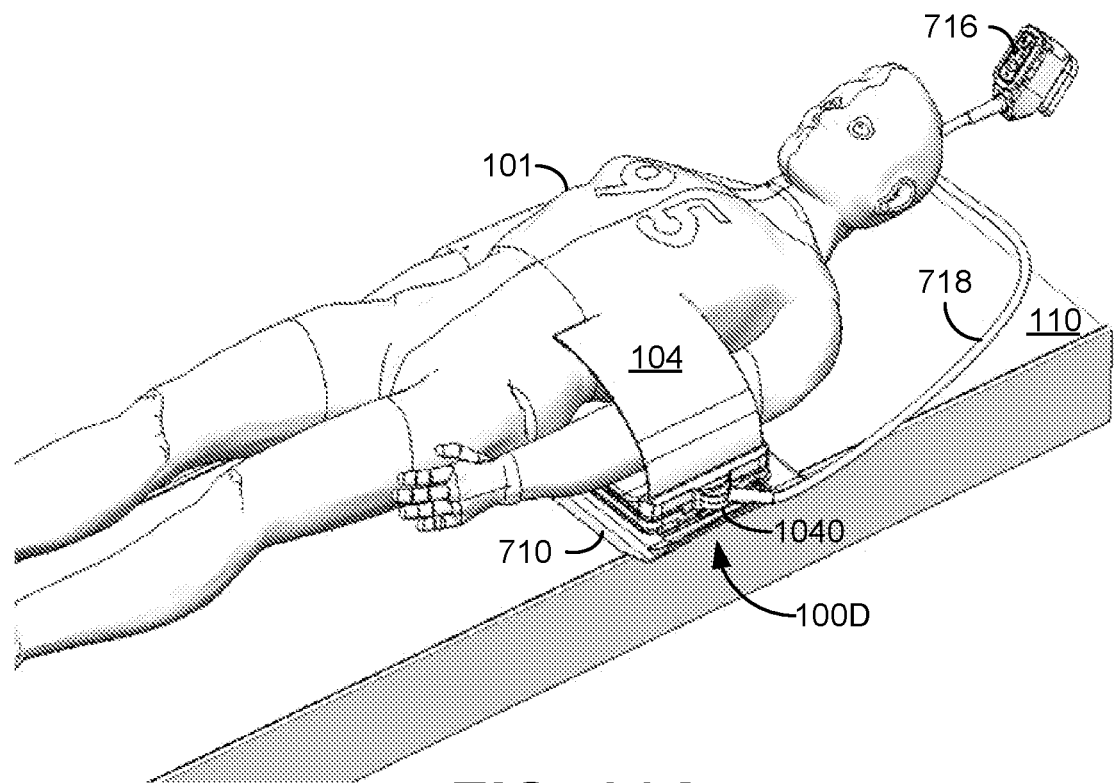
FIGS. 26A-26C illustrate views of some embodiments of an RF surface coil for general musculoskeletal scanning, placed on a patient table and configured to scan a left elbow anatomy.
Figure 26B:
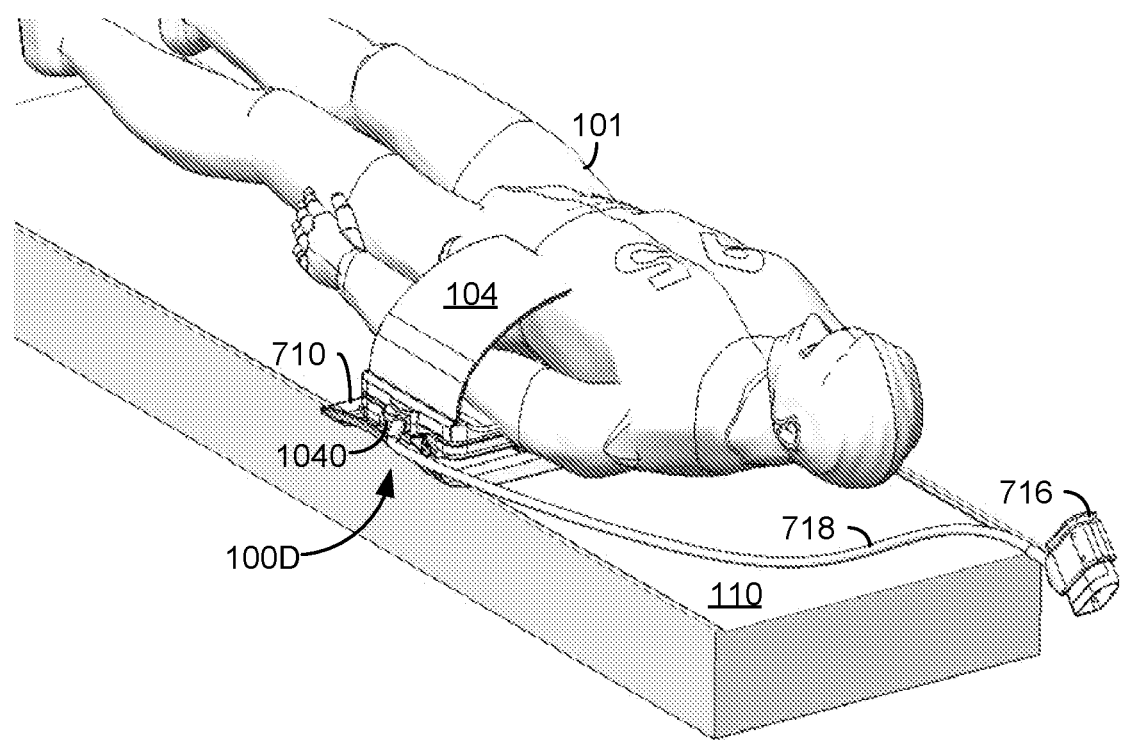
Figure 26C:
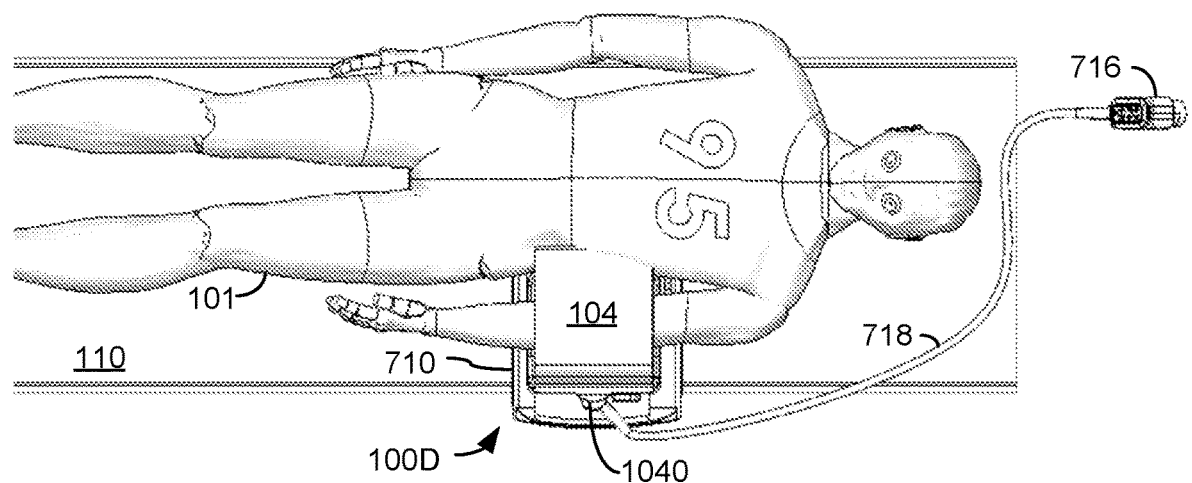

FIGS. 25A-25C illustrate views of some embodiments of the RF surface coil 100D placed on a patient table 110 and configured to scan a left shoulder anatomy of a patient 101. Similarly, FIGS. 26A-26C illustrate views of some embodiments of the RF surface coil 100D placed on the patient table 110 and configured to scan a left elbow anatomy of the patient 101. Other portions of the patient 101 anatomy, such as a hip, thigh, and the like, may be imaged using the RF surface coil 100D.

Figure 27:
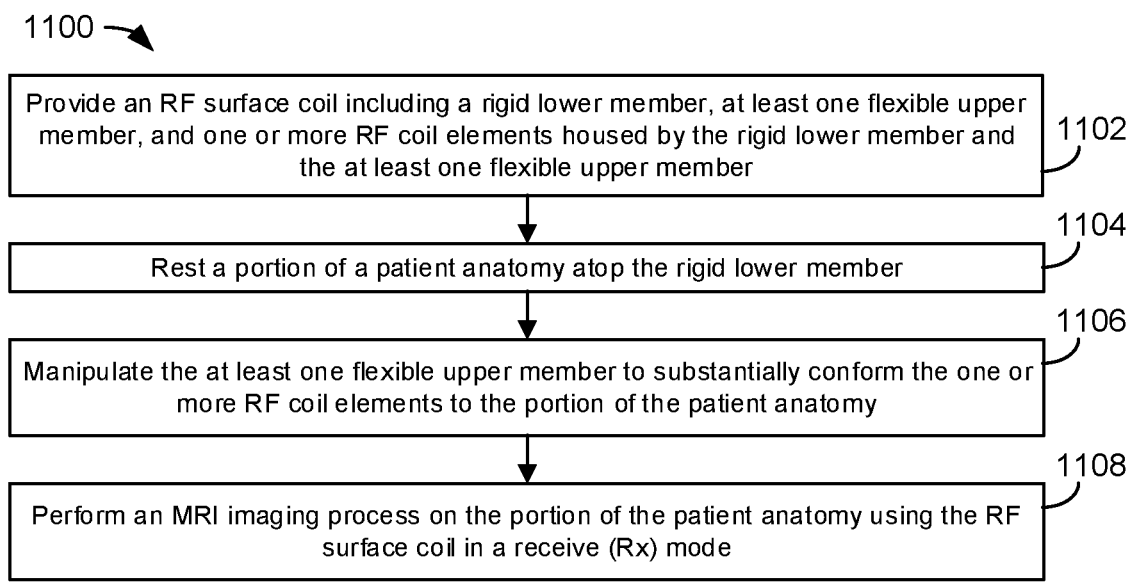
FIG. 27 illustrates a flow diagram of some embodiments of employing an RF surface coil to image a portion of a patient anatomy.

FIG. 27 illustrates a flow diagram of a method 1100 for imaging a portion of a patient anatomy (e.g., using one or more embodiments of an RF surface coil, as described herein). While method 1100 is described below in terms of a series of operations, in other embodiments, one or more of the operations may be omitted, other operations may be added, two or more operations may be combined into fewer operations or separated into a greater number of operations, and some operations may be performed in a different order from that indicated in FIG. 27.

In method 1100, at operation 1102, an RF surface coil (e.g., RF surface coil 100, 100A, 100B, 100C, or 100D) may be provided, in which the RF surface coil includes a rigid lower member, at least one flexible upper member, and one or more RF coil elements housed by the rigid lower member and the at least one flexible upper member. In some embodiments, the RF surface coil may be attached to or laid upon a patient table (e.g., patient table 110) of an MRI system, as discussed above. In addition, the RF surface coil may be positioned (e.g., located and/or oriented) to facilitate imaging of a portion of the patient anatomy, as described above.

At operation 1104, the portion of a patient anatomy (e.g., a knee, ankle, wrist, shoulder, elbow, or the like of a patient 101) to be imaged may be placed atop the rigid lower member. At operation 1106, the at least one flexible upper member may be manipulated to substantially conform the one or more RF coil elements to the portion of the patient anatomy. At operation 1108, an MRI imaging process may be performed on the portion of the patient anatomy using the RF surface coil in a receive (Rx) mode. In some embodiments, the MRI imaging process may further include using the RF surface coil in a transmit (Tx) mode, which may further enhance the quality of the resulting image of the patient anatomy.

Figure 28:
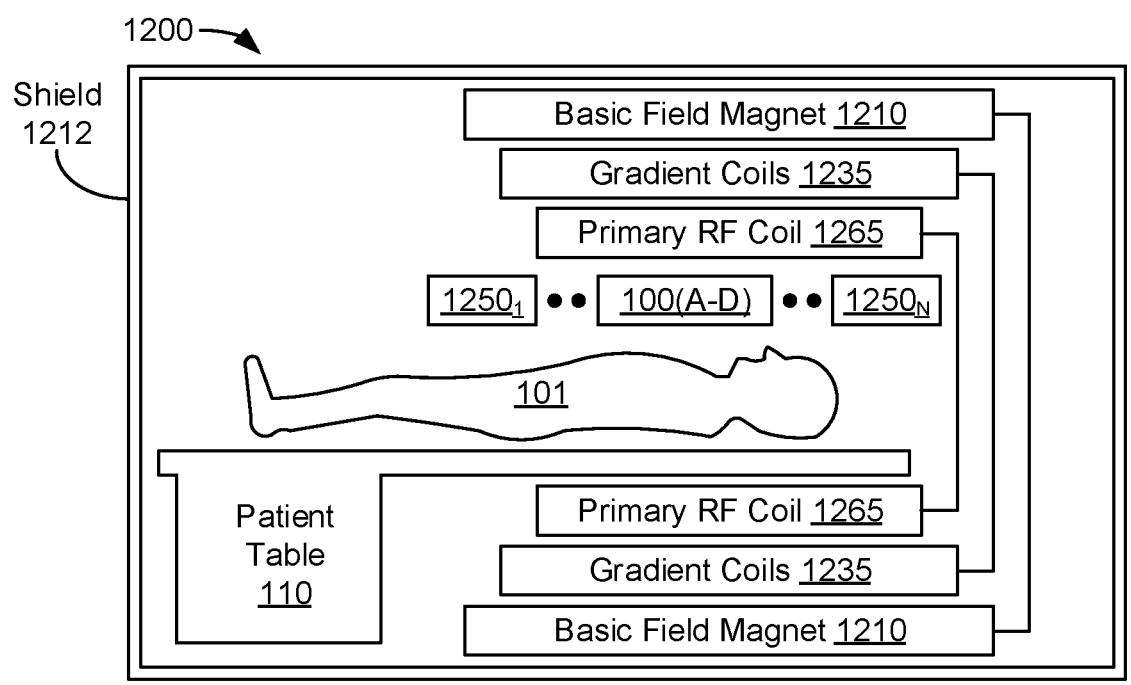
FIG. 28 illustrates a high-level view of some embodiments of a magnetic resonance imaging (MRI) system.

With reference to FIG. 28, a high-level view of some embodiments of an MRI system 1200 (e.g., serving as the MRI system mentioned above) according to aspects of the present disclosure is provided.

MRI system 1200 uses RF antennas, in the form of coils or coil elements, to transmit and receive RF pulses within a magnetic field (e.g., generated by a basic field magnet 1210). The received pulses are used to create images of tissue of a patient 101 (e.g., positioned on a patient table 110) to aid in the diagnosis of medical conditions. Generally, a shield 1212 may substantially contain the generated magnetic fields and RF pulses from the surrounding environment of MRI system 1200.

In some examples, MRI system 1200 may incorporate a whole-body coil (WBC) (e.g., primary RF coil 1265, operating in conjunction with gradient coils 1235) as a transmission device. However, the WBC may sometimes be used as a receive device. The WBC is intended for imaging large portions of the body. In lieu of the WBC, a smaller local MRI coil or RF antenna 1250 (e.g., one or more local antennas 1250₁, 1250₂ . . . 1250ₙ) may be employed to receive RF pulses from the anatomy being imaged. As indicated in FIG. 28, a particular type of local MRI coil or RF antenna 1250 may be the MRI (or RF) surface coil 100, 100A, 100B, 100C, or 100D placed close to a portion of the anatomy of patient 101, as discussed above with respect to FIGS. 1A-27. An RF surface coil 100 may use a plurality of RF coil elements (e.g., RF antennas).

Figure 29:
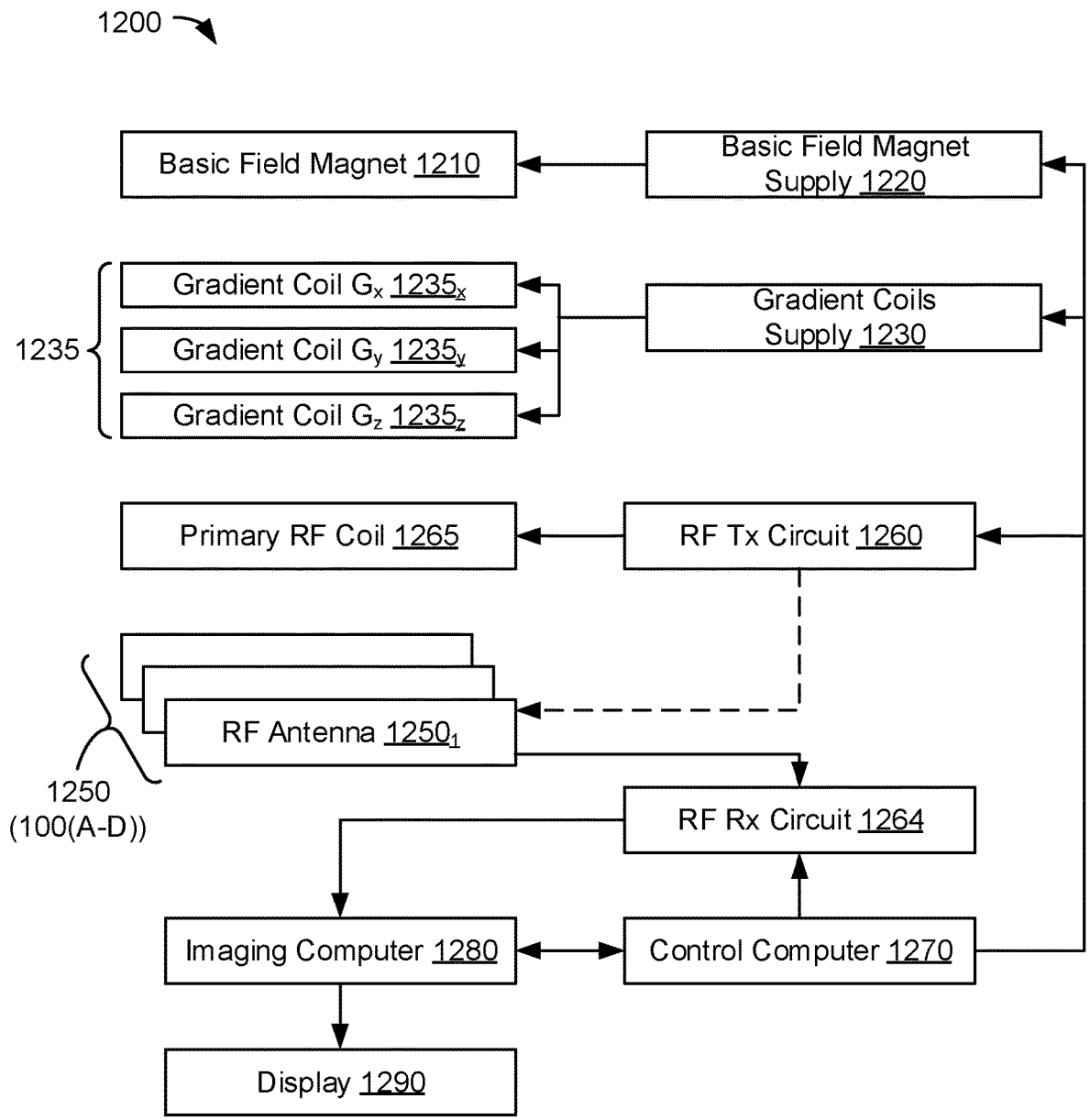
FIG. 29 illustrates a block diagram of some embodiments of an MRI system.

With reference to FIG. 29, a block diagram of some embodiments of the MRI system 1200 that can be configured with example MRI RF coils, coil channels, coil elements, coil arrays, or circuitry according to one or more embodiments described herein, is provided.

The MRI system 1200 includes the one or more basic field magnets 1210 and a basic field magnet supply 1220. Ideally, the basic field magnet(s) 1210 produce a uniform $B_0$ field. However, in practice, the $B_0$ field may not be uniform, and may vary over an object being imaged by the MRI system 1200. The MRI system 1200 can include gradient coils 1235 configured to emit gradient magnetic fields like $G_x$ (e.g., via an associated gradient coil 1235x), $G_y$ (e.g., via an associated gradient coil 1235y), and $G_z$ (e.g., via an associated gradient coil 1235z). The gradient coils 1235 can be controlled, at least in part, by a gradient coils supply 1230. In some examples, the timing, strength, and orientation of the gradient magnetic fields can be controlled, and thus selectively adapted during an MRI procedure.

The MRI system 1200 can include a primary RF coil 1265 configured to generate RF pulses. The primary RF coil 1265 can be a WBC. The primary RF coil 1265 can be, for example, a birdcage coil. The primary RF coil 1265 can be controlled, at least in part, by one or more RF transmission circuits 1260. The RF transmission circuit(s) 1260 can provide a signal to the primary RF coil 1265.

The MRI system 1200 can include a set of RF antennas 1250 (e.g., one or more RF antennas 1250₁-1250ₙ, which can be as described herein). The RF antennas 1250 can be configured to generate RF pulses and/or to receive resulting magnetic resonance signals from an object to which the RF pulses are directed. An RF antenna 1250 configured solely to generate RF pulses can be referred to herein as a Tx antenna (or coil or coil array), while an RF antenna 1250 configured solely to receive resulting magnetic resonance signals from an object to which the RF pulses are directed can be referred to herein as an Rx antenna (or coil or coil array). An RF antenna 1250 configured to both generate RF pulses and receive resulting magnetic resonance signals can be referred to herein as a Tx/Rx antenna (or coil or coil array). Unless otherwise indicated, antennas, coils, and coil arrays discussed herein can, in various embodiments, be any of a Tx antenna/coil/coil array, an Rx antenna/coil/coil array, or a Tx/Rx antenna/coil/coil array.

In some embodiments, the RF antennas 1250 can be configured to inductively couple with the primary RF coil 1265 and generate RF pulses and to receive resulting magnetic resonance signals from an object to which the RF pulses are directed. In other embodiments, the RF antennas 1250 can be electrically coupled to a power source (e.g., the RF transmission circuit(s) 1260) that can drive the RF antennas 1250 to generate RF pulses, and the RF antennas 1250 can also be configured to receive resulting magnetic resonance signals from an object to which the RF pulses are directed. In one embodiment, one or more members of the set of RF antennas 1250 can be fabricated from flexible coaxial cable or other conductive material. The set of RF antennas 1250 can be connected with one or more RF receive circuits 1264.

The gradient coils supply 1230 and the RF transmission circuit(s) 1260 can be controlled, at least in part, by a control computer 1270. The magnetic resonance signals received from the set of RF antennas 1250 can be employed to generate an image, and thus can be subject to a transformation process like a two-dimensional fast Fourier transform (FFT) that generates pixelated image data. The transformation can be performed by an image computer 1280 or other similar processing device. The image data can then be shown on a display 1290. The RF receive circuit(s) 1264 can be connected with the control computer 1270 or the image computer 1280.

While FIG. 29 illustrates an example MRI system 1200 that includes various components connected in various ways, it is to be appreciated that other MRI systems can include other components connected in other ways, and can be employed in connection with various embodiments discussed herein.

In one embodiment, the MRI system 1200 includes the control computer 1270. In one example, a member of the set of RF antennas 1250 can be individually controllable by the control computer 1270. The control computer 1270 can provide a DC bias current, or control a DC bias control circuit to control the application of a DC bias current, to PIN diodes that can be part of the RF antennas 1250 and/or the primary RF coil 1265.

In some embodiments, a member of the set of RF antennas 1250 can be or include any example Tx coil, MRI RF coil (e.g., surface coil), coil element, or the like described herein. In some embodiments, one, some, or all members of the set of RF antennas 1250 can be or correspond to any example RF coil element as in FIGS. 2A to 5B, any RF coil element array as in FIGS. 6A to 6E, or any RF surface coil as in FIGS. 7A to 26C.

An MRI system can include, among other components, a controller (e.g., the control computer 1270) and an RF coil (e.g., the primary RF coil 1265) operably connected to the controller. The controller can provide the RF coil with a current, a voltage, or a control signal. The RF coil can be a WBC. The RF coil can inductively couple with and wirelessly drive any example RF coil element as in FIGS. 2A to 5B, any RF coil element array as in FIGS. 6A to 6E, or any RF surface coil as in FIGS. 7A to 26C.

In an Example 1, an RF surface coil for an MRI system includes: a rigid lower member; at least one flexible upper member mechanically coupled to the rigid lower member; and one or more RF coil elements housed by the rigid lower member and the at least one flexible upper member, the at least one flexible upper member being dimensioned and manipulable to substantially conform the one or more RF coil elements to a portion of a patient anatomy to be imaged by the MRI system.

In an Example 2 that depends on Example 1, the at least one flexible upper member includes a first flexible upper member and a second flexible upper member; and the first flexible upper member and the second flexible upper member, when manipulated to substantially conform the one or more RF coil elements to the portion of the patient anatomy, at least partially overlap.

In an Example 3 that depends on any one of Examples 1 and 2, the rigid lower member is shaped to approximately match a shape of the portion of the patient anatomy to be imaged.

In an Example 4 that depends on any one of Examples 1-3, the RF surface coil further includes a cable assembly electrically coupled to the one or more RF coil elements via the rigid lower member to interface the one or more RF coil elements with the MRI system.

In an Example 5 that depends on Example 4, the RF surface coil further includes a pivoting housing pivotally coupling the cable assembly to the rigid lower member about a vertical axis.

In an Example 6 that depends on any one of Examples 1-5, each of the at least one flexible upper member further includes a flexible substrate to which at least one of the one or more RF coil elements are affixed.

In an Example 7 that depends on Example 6, the at least one of the one or more RF coil elements is woven into the flexible substrate.

In an Example 8 that depends on Example 6, the at least one flexible upper member further includes a retaining member that overlays the at least one of the one or more RF coil elements and the flexible substrate; and the retaining member is bonded to the flexible substrate to affix the at least one of the one or more RF coil elements to the flexible substrate.

In an Example 9 that depends on Example 6, the at least one flexible upper member further includes a plurality of fasteners that fasten the at least one of the one or more RF coil elements to the flexible substrate.

In an Example 10 that depends on Example 6, each of the at least one flexible upper member further includes at least one flexible flame barrier layer covering the flexible substrate.

In an Example 11 that depends on Example 6, the RF surface coil further includes an electronic circuit mounted on the flexible substrate to interface the at least one of the one or more RF coil elements to the MRI system.

In an Example 12 that depends on any one of Examples 1-11, the at least one flexible upper member includes an outer layer configured to cover the one or more RF coil elements; the rigid lower member includes an outer enclosure and an internal bracket; and the outer layer is pressed between the outer enclosure and the internal bracket to inhibit fluid ingress between the at least one flexible upper member and the lower rigid member.

In an Example 13 that depends on any one of Examples 1-12, the RF surface coil further includes a baseframe mechanically coupled to the rigid lower member, wherein the baseframe is configured to attach the RF surface coil to a patient table of the MRI system.

In an Example 14 that depends on Example 13, the baseframe includes a coil-positioning structure to mechanically couple the rigid lower member to the baseframe at a plurality of positions relative to the baseframe; and the plurality of positions includes at least one of two or more different locations on a horizontal surface of the baseframe or two or more different orientations of the rigid lower member about an axis normal to the horizontal surface of the baseframe.

In an Example 15 that depends on Example 13, the rigid lower member includes a coil-positioning structure that couples the rigid lower member to the baseframe; and the rigid lower member is configured to pivot relative to the coil-positioning structure about an axis parallel to a horizontal surface of the baseframe.

In an Example 16 that depends on any one of Examples 1-15, a size of the one or more RF coil elements is based on a size of one or more features of the portion of the patient anatomy to be imaged.

In an Example 17, an MRI system includes: a patient table; and an RF surface coil that includes: a rigid lower member: at least one flexible upper member mechanically coupled to the rigid lower member; one or more RF coil elements housed by the rigid lower member and the at least one flexible upper member, the at least one flexible upper member being dimensioned and manipulable to substantially conform the one or more RF coil elements to a portion of a patient anatomy to be imaged by the MRI system; and a baseframe mechanically coupled to the rigid lower member at a selected one of a plurality of positions relative to the baseframe and releasably attached to the patient table.

In an Example 18 that depends on Example 17, the RF surface coil further includes a cable assembly electrically coupling the one or more RF coil elements via the rigid lower member to at least one of an RF receive circuit or an RF transmit circuit of the MRI system.

In an Example 19, a method includes: providing a radio frequency (RF) surface coil for magnetic resonance imaging (MRI), the RF surface coil including: a rigid lower member; at least one flexible upper member mechanically coupled to the rigid lower member; and one or more RF coil elements housed by the rigid lower member and the at least one flexible upper member; resting a portion of a patient anatomy atop the rigid lower member; manipulating the at least one flexible upper member to substantially conform the one or more RF coil elements to the portion of the patient anatomy; and performing an MRI imaging process on the portion of the patient anatomy using the RF surface coil in a receive (Rx) mode.

In an Example 20 that depends on Example 19, performing the MRI imaging process further includes using the RF surface coil in a transmit (Tx) mode.

The following includes definitions of selected terms employed herein. The definitions include various examples or forms of components that fall within the scope of a term and that may be used for implementation. The examples are not intended to be limiting. Both singular and plural forms of terms may be within the definitions.

The terminology used herein is for the purpose of describing particular embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which embodiments belong. It will be further understood that terms (e.g., those defined in commonly used dictionaries) should be interpreted as having a meaning that is consistent with their meaning in the context of the relevant art and will not be interpreted in an idealized or overly formal sense unless expressly so defined herein.

In the above description, some components may be displayed in multiple figures carrying the same reference signs and/or names but may not be described multiple times in detail. A detailed description of a component may then apply to that component for all its occurrences. Further, numerical designations (e.g., first, second, third, etc.) may be used for clarity to distinguish between components of the same type. However, it is to be appreciated that the numerical designation may vary for components displayed in multiple figures, depending upon context. For example, a component referred to as third in one figure, may be referred to as fourth in another figure if another component of the same type already has the designation of third.

The detailed descriptions presented herein may be presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on refer to actions and processes of a computer system, logic, processor, or similar electronic device that manipulates and transforms data represented as physical and/or electronic quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

What is claimed is:

1. A radio frequency (RF) surface coil for a magnetic resonance imaging (MRI) system, the RF surface coil comprising:
    a rigid lower member;
    at least one flexible upper member mechanically coupled to the rigid lower member; and
    one or more RF coil elements housed by the rigid lower member and the at least one flexible upper member, the at least one flexible upper member being dimensioned and manipulable to substantially conform the one or more RF coil elements to a portion of a patient anatomy to be imaged by the MRI system, wherein
    the at least one flexible upper member comprises an outer layer configured to cover the one or more RF coil elements,
    the rigid lower member comprises an outer enclosure and an internal bracket, and
    the outer layer is pressed between the outer enclosure and the internal bracket to inhibit fluid ingress between the at least one flexible upper member and the lower rigid member.

2. The RF surface coil of claim 1, wherein:
    the at least one flexible upper member comprises a first flexible upper member and a second flexible upper member; and
    the first flexible upper member and the second flexible upper member, when manipulated to substantially conform the one or more RF coil elements to the portion of the patient anatomy, at least partially overlap.

3. The RF surface coil of claim 1, wherein the rigid lower member is shaped to approximately match a shape of the portion of the patient anatomy to be imaged.

4. The RF surface coil of claim 1, further comprising:
a cable assembly electrically coupled to the one or more RF coil elements via the rigid lower member to interface the one or more RF coil elements with the MRI system.

5. The RF surface coil of claim 4, further comprising:
a pivoting housing pivotally coupling the cable assembly to the rigid lower member about a vertical axis.

6. The RF surface coil of claim 1, wherein each of the at least one flexible upper member further comprises a flexible substrate to which at least one of the one or more RF coil elements are affixed.

7. The RF surface coil of claim 6, wherein the at least one of the one or more RF coil elements is woven into the flexible substrate.

8. The RF surface coil of claim 6, wherein:
the at least one flexible upper member further comprises a retaining member that overlays the at least one of the one or more RF coil elements and the flexible substrate; and
the retaining member is bonded to the flexible substrate to affix the at least one of the one or more RF coil elements to the flexible substrate.

9. The RF surface coil of claim 6, wherein:
the at least one flexible upper member further comprises a plurality of fasteners that fasten the at least one of the one or more RF coil elements to the flexible substrate.

10. The RF surface coil of claim 6, wherein:
each of the at least one flexible upper member further comprises at least one flexible flame barrier layer covering the flexible substrate.

11. The RF surface coil of claim 6, further comprising:
an electronic circuit mounted on the flexible substrate to interface the at least one of the one or more RF coil elements to the MRI system.

12. The RF surface coil of claim 1, further comprising:
a baseframe mechanically coupled to the rigid lower member, wherein the baseframe is configured to attach the RF surface coil to a patient table of the MRI system.

13. The RF surface coil of claim 12, wherein:
the baseframe comprises a coil-positioning structure to mechanically couple the rigid lower member to the baseframe at a plurality of positions relative to the baseframe; and
the plurality of positions comprises at least one of two or more different locations on a horizontal surface of the baseframe or two or more different orientations of the rigid lower member about an axis normal to the horizontal surface of the baseframe.

14. The RF surface coil of claim 12, wherein:
the rigid lower member comprises a coil-positioning structure that couples the rigid lower member to the baseframe; and
the rigid lower member is configured to pivot relative to the coil-positioning structure about an axis parallel to a horizontal surface of the baseframe.

15. The RF surface coil of claim 1, wherein:
a size of the one or more RF coil elements is based on a size of one or more features of the portion of the patient anatomy to be imaged.

16. The RF surface coil of claim 1, wherein:
an opening of the outer layer is slid over an opening of the internal bracket; and
the internal bracket presses the outer layer against an interior surface of the outer enclosure.

17. A magnetic resonance imaging (MRI) system comprising:
a patient table; and
a radio frequency (RF) surface coil that comprises:
a rigid lower member;
at least one flexible upper member mechanically coupled to the rigid lower member;
one or more RF coil elements housed by the rigid lower member and the at least one flexible upper member, the at least one flexible upper member being dimensioned and manipulable to substantially conform the one or more RF coil elements to a portion of a patient anatomy to be imaged by the MRI system,
wherein
the at least one flexible upper member comprises an outer layer configured to cover the one or more RF coil elements,
the rigid lower member comprises an outer enclosure and an internal bracket, and
the outer layer is pressed between the outer enclosure and the internal bracket to inhibit fluid ingress between the at least one flexible upper member and the lower rigid member; and
a baseframe mechanically coupled to the rigid lower member at a selected one of a plurality of positions relative to the baseframe and releasably attached to the patient table.

18. The MRI system of claim 17, further comprising:
a cable assembly electrically coupling the one or more RF coil elements via the rigid lower member to at least one of an RF receive circuit or an RF transmit circuit of the MRI system.

19. A method comprising:
providing a radio frequency (RF) surface coil for magnetic resonance imaging (MRI), the RF surface coil comprising:
a rigid lower member;
at least one flexible upper member mechanically coupled to the rigid lower member; and
one or more RF coil elements housed by the rigid lower member and the at least one flexible upper member, wherein
the at least one flexible upper member comprises an outer layer configured to cover the one or more RF coil elements,
the rigid lower member comprises an outer enclosure and an internal bracket, and
the outer layer is pressed between the outer enclosure and the internal bracket to inhibit fluid ingress between the at least one flexible upper member and the lower rigid member;
resting a portion of a patient anatomy atop the rigid lower member;
manipulating the at least one flexible upper member to substantially conform the one or more RF coil elements to the portion of the patient anatomy; and
performing an MRI imaging process on the portion of the patient anatomy using the RF surface coil in a receive (Rx) mode.

20. The method of claim 19, wherein performing the MRI imaging process further includes using the RF surface coil in a transmit (Tx) mode.

* * * * *